US011504191B2

(12) United States Patent
Mccloud et al.

(10) Patent No.: US 11,504,191 B2
(45) Date of Patent: Nov. 22, 2022

(54) GRAPHICAL USER INTERFACE FOR A ROBOTIC SURGICAL SYSTEM

(71) Applicant: Titan Medical Inc., Toronto (CA)

(72) Inventors: Jefferson C. Mccloud, Providence, RI (US); Daniel Bacher, Providence, RI (US)

(73) Assignee: TITAN MEDICAL INC., Toronto (CA)

( * ) Notice: Subject to any disclaimer, the term of this patent is extended or adjusted under 35 U.S.C. 154(b) by 648 days.

(21) Appl. No.: 15/780,593

(22) PCT Filed: Jan. 19, 2017

(86) PCT No.: PCT/CA2017/000011
§ 371 (c)(1),
(2) Date: May 31, 2018

(87) PCT Pub. No.: WO2017/124177
PCT Pub. Date: Jul. 27, 2017

(65) Prior Publication Data
US 2018/0353245 A1    Dec. 13, 2018

Related U.S. Application Data

(60) Provisional application No. 62/280,334, filed on Jan. 19, 2016.

(51) Int. Cl.
*A61B 34/00* (2016.01)
*A61B 34/30* (2016.01)
(Continued)

(52) U.S. Cl.
CPC .............. *A61B 34/25* (2016.02); *A61B 34/20* (2016.02); *A61B 34/30* (2016.02); *A61B 34/76* (2016.02);
(Continued)

(58) Field of Classification Search
None
See application file for complete search history.

(56) References Cited

U.S. PATENT DOCUMENTS

| 5,402,801 A | 4/1995 | Taylor |
| 6,351,661 B1 | 2/2002 | Cosman |

(Continued)

FOREIGN PATENT DOCUMENTS

| CN | 1599916 A | 3/2005 |
| CN | 101557768 A | 10/2009 |

(Continued)

OTHER PUBLICATIONS

Supplementary European Search Report in Application No. EP 17740924, dated Nov. 28, 2018, in 8 pages.

(Continued)

*Primary Examiner* — Katherine L Fernandez
(74) *Attorney, Agent, or Firm* — Knobbe, Martens, Olson & Bear LLP

(57) ABSTRACT

A method, apparatus and computer readable medium for schematically representing a spatial position of an instrument used in a robotic surgery system is disclosed. The instrument includes an end effector coupled to a positioning device for spatially positioning the end effector in a surgical workspace in response to input signals generated by movement of a hand controller of an input device in an input device workspace. The method involves causing a processor circuit to calculate a current three-dimensional spatial position of the instrument within the surgical workspace for current input signals received from the input device. The method also involves causing the processor circuit to generate display signals for displaying a graphical depiction of the surgical workspace on a display in communication with the processor circuit, the graphical depiction including a planar representation includes an instrument movement (Continued)

region having a boundary indicating limitations to transverse movement of the instrument within the surgical workspace, and a two-dimensional projection of the current spatial position of the positioning device and the end effector onto the planar representation.

22 Claims, 11 Drawing Sheets

(51) Int. Cl.
   *A61B 34/20* (2016.01)
   *A61B 17/00* (2006.01)
   *A61B 90/00* (2016.01)

(52) U.S. Cl.
   CPC ............. *A61B 2017/00314* (2013.01); *A61B 2017/00323* (2013.01); *A61B 2017/00973* (2013.01); *A61B 2034/742* (2016.02); *A61B 2090/371* (2016.02)

(56) References Cited

U.S. PATENT DOCUMENTS

| | | |
|---|---|---|
| 8,594,841 B2 | 11/2013 | Zhao et al. |
| 2004/0152970 A1 | 8/2004 | Hunter |
| 2007/0043338 A1* | 2/2007 | Moll ............... A61B 17/062 606/1 |
| 2007/0088340 A1 | 4/2007 | Brock et al. |
| 2009/0326318 A1* | 12/2009 | Tognaccini ........... A61B 34/37 600/104 |
| 2009/0326365 A1 | 12/2009 | Goldenberg et al. |
| 2010/0198200 A1 | 8/2010 | Horvath |
| 2013/0060278 A1* | 3/2013 | Bozung ............. A61B 17/3403 606/205 |
| 2013/0245375 A1 | 9/2013 | DiMaio et al. |
| 2014/0222023 A1* | 8/2014 | Kim ................... A61B 34/30 606/130 |
| 2014/0276943 A1* | 9/2014 | Bowling ............... A61B 90/03 606/130 |
| 2017/0319283 A1* | 11/2017 | Suresh ................. A61B 34/37 |

FOREIGN PATENT DOCUMENTS

| | | |
|---|---|---|
| CN | 104582628 A | 4/2015 |
| CN | 105025836 A | 11/2015 |
| CN | 105167793 A | 12/2015 |
| EP | 2289453 A2 | 3/2011 |
| EP | 2 754 383 A2 | 7/2014 |
| JP | 2001-104333 A | 4/2001 |
| JP | 2002-253574 | 9/2002 |
| JP | 2002253574 A | 9/2002 |
| JP | 2007527296 A | 9/2007 |
| JP | 2014097431 A | 5/2014 |
| JP | 2015-502180 | 1/2015 |
| JP | 2015502180 A | 1/2015 |
| JP | 2016512084 A | 4/2016 |
| WO | WO2005084570 A1 | 9/2005 |
| WO | WO 2007/117297 A2 | 10/2007 |
| WO | WO2007117297 A2 | 10/2007 |
| WO | WO2009120946 A2 | 10/2009 |
| WO | WO 2010/151438 A1 | 12/2010 |
| WO | WO2010151438 A1 | 12/2010 |
| WO | WO 2013/033566 | 3/2013 |
| WO | WO 2014/165060 | 10/2014 |
| WO | WO2014165060 A2 | 10/2014 |
| WO | WO2014186715 A1 | 11/2014 |
| WO | WO 2014/194167 | 12/2014 |

OTHER PUBLICATIONS

English translation of Chinese First Office Action issued in Application No. 201780005500.6 dated Jun. 3, 2020.
International Search Report received in PCT Application No. PCT/CA2017/000011, dated Apr. 26, 2017.
Written Opinion received in PCT Application No. PCT/CA2017/000011, dated Apr. 26, 2017.
Hansen Medical Inc, "3 Sensen X System Overview VD0045 Rev A Sensei X LIM MP4,", Jun. 28, 2014, https://www.youtube.com/watch?v=yg2YQcsxQ6k.

* cited by examiner

GRAPHICAL USER INTERFACE FOR A ROBOTIC SURGICAL SYSTEM

CROSS-REFERENCE TO RELATED APPLICATION

This application is a U.S. National Phase Application under 35 U.S.C. 371 of International Application No. PCT/CA2017/000011 filed on Jan. 19, 2017 and published as WO 2017/124177 A1 on Jul. 27, 2017. This application claims priority to U.S. Provisional Application No. 62/280,334, filed Jan. 19, 2016. The entire disclosures of all of the above applications are incorporated herein by reference.

BACKGROUND

1. Field

This disclosure relates to surgical robotic systems and more particularly to schematically representing a spatial position of an instrument used in a robotic surgery system.

2. Description of Related Art

In robotic surgery systems, a graphical user interface is generally used to provide alerts and notifications that provide the surgeon with sufficient information to perform surgical tasks. It is common to provide an image of the surgical site within a patient's body cavity that shows both the area where the surgical tasks are being performed and often a portion of the surgical instruments that are deployed to perform the tasks.

SUMMARY

In accordance with one disclosed aspect there is provided a method for schematically representing a spatial position of an instrument used in a robotic surgery system, the instrument including an end effector coupled to a positioning device for spatially positioning the end effector in a surgical workspace in response to input signals generated by movement of a hand controller of an input device in an input device workspace. The method involves causing a processor circuit to calculate a current three-dimensional spatial position of the instrument within the surgical workspace for current input signals received from the input device. The method also involves causing the processor circuit to generate display signals for displaying a graphical depiction of the surgical workspace on a display in communication with the processor circuit, the graphical depiction including a planar representation includes an instrument movement region having a boundary indicating limitations to transverse movement of the instrument within the surgical workspace, and a two-dimensional projection of the current spatial position of the positioning device and the end effector onto the planar representation.

The end effector may be represented by an indicator and the positioning device may be represented by an area corresponding to two dimensional projected extents of at least a portion of the positioning device.

The method may involve generating the boundary by defining a three-dimensional boundary within the surgical workspace, and generating a two-dimensional projection of the three-dimensional boundary onto the planar representation.

The boundary of the instrument movement region may further include at least one keep-out zone identifying a further limitation to movement of the instrument within the surgical workspace.

The keep-out zone may be defined based on at least one of input received from an operator at an input device and patient imaging data received at the processor circuit.

The method may further involve, in response to a determination that the instrument is proximate the boundary of the instrument movement region, causing the processor circuit to display an active constraint indication at the boundary.

The robotic surgery system may include a plurality of instruments within the surgical workspace and displaying the graphical depiction may involve displaying a graphical depiction for each of the plurality of instruments.

Displaying the graphical depiction may include displaying the graphical depiction at a peripheral region of the display.

The graphical depiction may further include an instrument depth range indicating limitations to axial movement of the instrument into the surgical workspace, an indicator representing a current depth of the end effector within the instrument depth range, and an input device depth range representing a portion of the instrument depth range that is accessible for a current mapping between the input device workspace and the surgical workspace.

The method may further involve, in response to a determination that the end effector is proximate an end of the input device depth range, causing the processor circuit to display an active constraint indication.

The method may involve receiving an enablement signal at the processor circuit, the enablement signal having an active state and an inactive state, the active state permitting movement of the instrument in response to the input signals and the inactive state inhibiting movement of the instrument to facilitate repositioning of the hand controller within the input device workspace, and the method may further involve in response to the enablement signal transitioning from the active to the in-active state, causing the processor circuit to generate display signals for displaying a current hand controller position indicator on the graphical depiction as offset from the two-dimensional projection of the current spatial position of the end effector, and in response to the enablement signal transitioning from the inactive to the active state, discontinuing display of the current hand controller position indicator.

The input signals produced by the input device may include a rotation signal defining a current rotation of the hand controller, the rotation signal being operable to cause rotation of the end effector in the surgical workspace and the graphical depiction may include an instrument rotation range indicating limitations on rotational movement of the instrument, an indicator representing a current rotation of the end effector, and an input device rotation range representing a portion of the instrument rotation range that is accessible for a current mapping between the input device workspace and the surgical workspace.

The method may involve receiving an enablement signal at the processor circuit, the enablement signal having an active state and an inactive state, the active state permitting movement of the instrument in response to the input signals and the inactive state inhibiting movement of the instrument to facilitate repositioning of the hand controller within the input device workspace, and the method may further involve in response to the enablement signal transitioning from the active to the in-active state, causing the processor circuit to generate display signals for displaying a current hand controller rotation indicator on the graphical depiction as offset from the indicator representing a current rotation of the end effector, and in response to the enablement signal transitioning from the inactive to the active state, discontinuing display of current hand controller rotation indicator.

In accordance with another disclosed aspect there is provided an apparatus for schematically representing a spatial position of an instrument used in a robotic surgery system, the instrument including an end effector coupled to a positioning device for spatially positioning the end effector in a surgical workspace in response to input signals generated by movement of a hand controller of an input device in an input device workspace. The apparatus includes a processor circuit operably configured to calculate a current three-dimensional spatial position of the instrument within the surgical workspace for current input signals received from the input device, and to generate display signals for displaying a graphical depiction of the surgical workspace on a display in communication with the processor circuit. The graphical depiction includes a planar representation including an instrument movement region having a boundary indicating limitations to transverse movement of the instrument within the surgical workspace, and a two-dimensional projection of the current spatial position of the positioning device and the end effector onto the planar representation.

The processor circuit may be operably configured to display an active constraint indication at the boundary in response to a determination that the instrument is proximate the boundary of the instrument movement region.

The graphical depiction may further include an instrument depth range indicating limitations to axial movement of the instrument into the surgical workspace, an indicator representing a current depth of the end effector within the instrument depth range, and an input device depth range representing a portion of the instrument depth range that is accessible for a current mapping between the input device workspace and the surgical workspace.

The processor circuit may be operably configured to display an active constraint indication in response to a determination that the end effector is proximate an end of the input device depth range.

The processor circuit may be operably configured to receive an enablement signal at the processor circuit, the enablement signal having an active state and an inactive state, the active state permitting movement of the instrument in response to the input signals and the inactive state inhibiting movement of the instrument to facilitate repositioning of the hand controller within the input device workspace, the processor circuit being operably configured to, in response to the enablement signal transitioning from the active to the in-active state, generate display signals for displaying a current hand controller position indicator on the graphical depiction as offset from the two-dimensional projection of the current spatial position of the end effector, and in response to the enablement signal transitioning from the inactive to the active state, discontinue display of the current hand controller position indicator.

The input signals produced by the input device include a rotation signal defining a current rotation of the hand controller, the rotation signal being operable to cause rotation of the end effector in the surgical workspace and the graphical depiction may include an instrument rotation range indicating limitations on rotational movement of the instrument, an indicator representing a current rotation of the end effector, and an input device rotation range representing a portion of the instrument rotation range that is accessible for a current mapping between the input device workspace and the surgical workspace.

The processor circuit may be operably configured to receive an enablement signal at the processor circuit, the enablement signal having an active state and an inactive state, the active state permitting movement of the instrument in response to the input signals and the inactive state inhibiting movement of the instrument to facilitate repositioning of the hand controller within the input device workspace, and the processor circuit may be operably configured to, in response to the enablement signal transitioning from the active to the in-active state, generate display signals for displaying a current hand controller rotation indicator on the graphical depiction as offset from the indicator representing a current rotation of the end effector, and in response to the enablement signal transitioning from the inactive to the active state, discontinue display of current hand controller rotation indicator.

In accordance with another disclosed aspect there is provided a computer readable medium encoded with codes for directing a processor circuit of a robotic surgery system to represent a spatial position of an instrument used in a robotic surgery system, the instrument including an end effector coupled to a positioning device for spatially positioning the end effector in a surgical workspace in response to input signals generated by movement of a hand controller of an input device in an input device workspace. The codes direct the processor circuit to calculate a current three-dimensional spatial position of the instrument within the surgical workspace for current input signals received from the input device, and to generate display signals for displaying a graphical depiction of the surgical workspace on a display in communication with the processor circuit, the graphical depiction including a planar representation including an instrument movement region having a boundary indicating limitations to transverse movement of the instrument within the surgical workspace, and a two-dimensional projection of the current spatial position of the positioning device and the end effector onto the planar representation.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
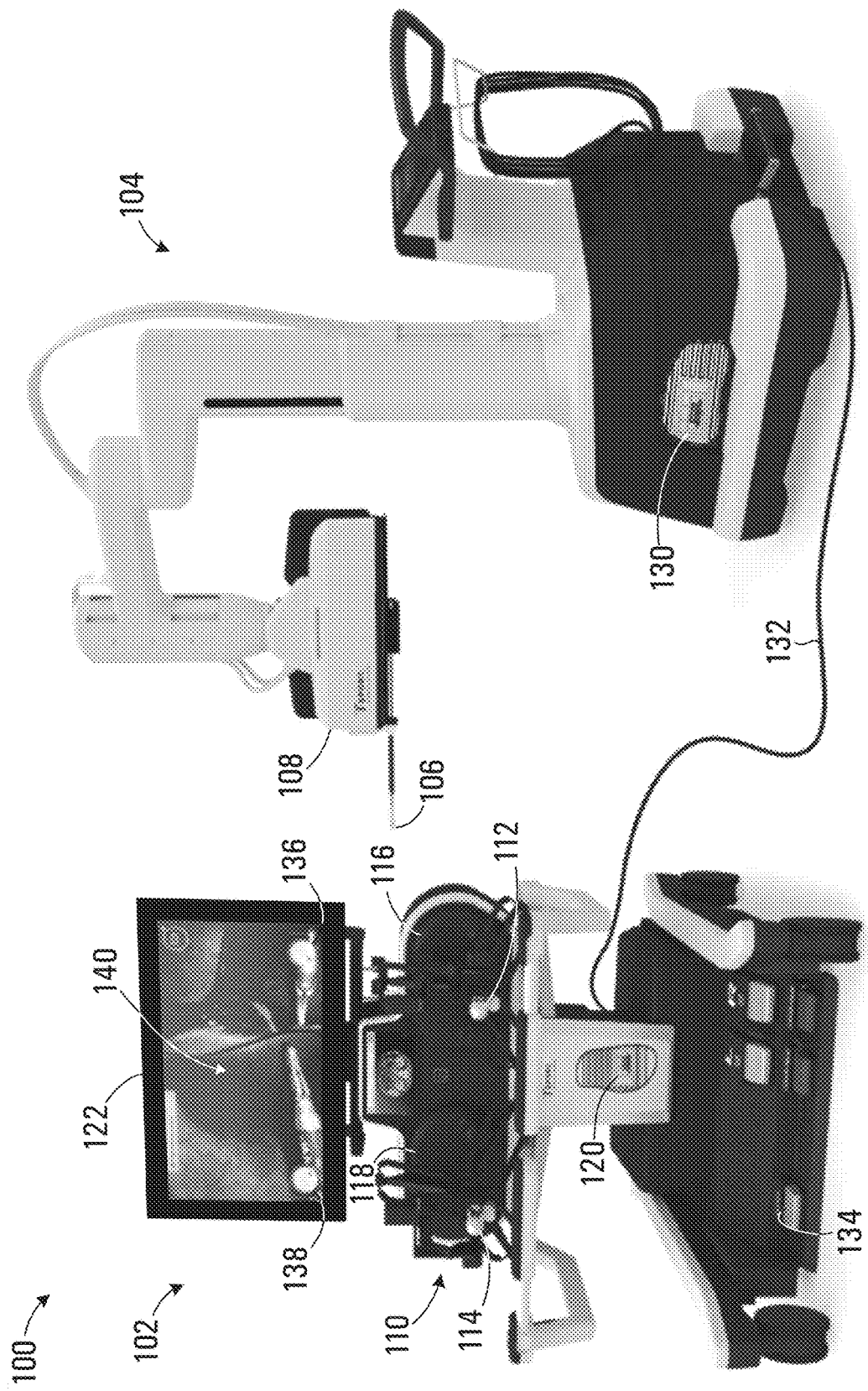
FIG. 1 is a perspective view of a robotic surgery system.

Referring to FIG. 1, a robotic surgery system is shown generally at 100. The system 100 includes a workstation 102 and an instrument cart 104. The instrument cart 104 includes at least one instrument 106 mounted on a moveable instrument mount 108 that houses an instrument drive for manipulating the instrument. The workstation 102 includes an input device 110 for use by a surgeon for controlling the instrument 106 via the instrument drive to perform surgical operations on a patient. The input device 110 may be implemented using a haptic interface available from Force Dimension, of Switzerland, for example.

Figure 2:
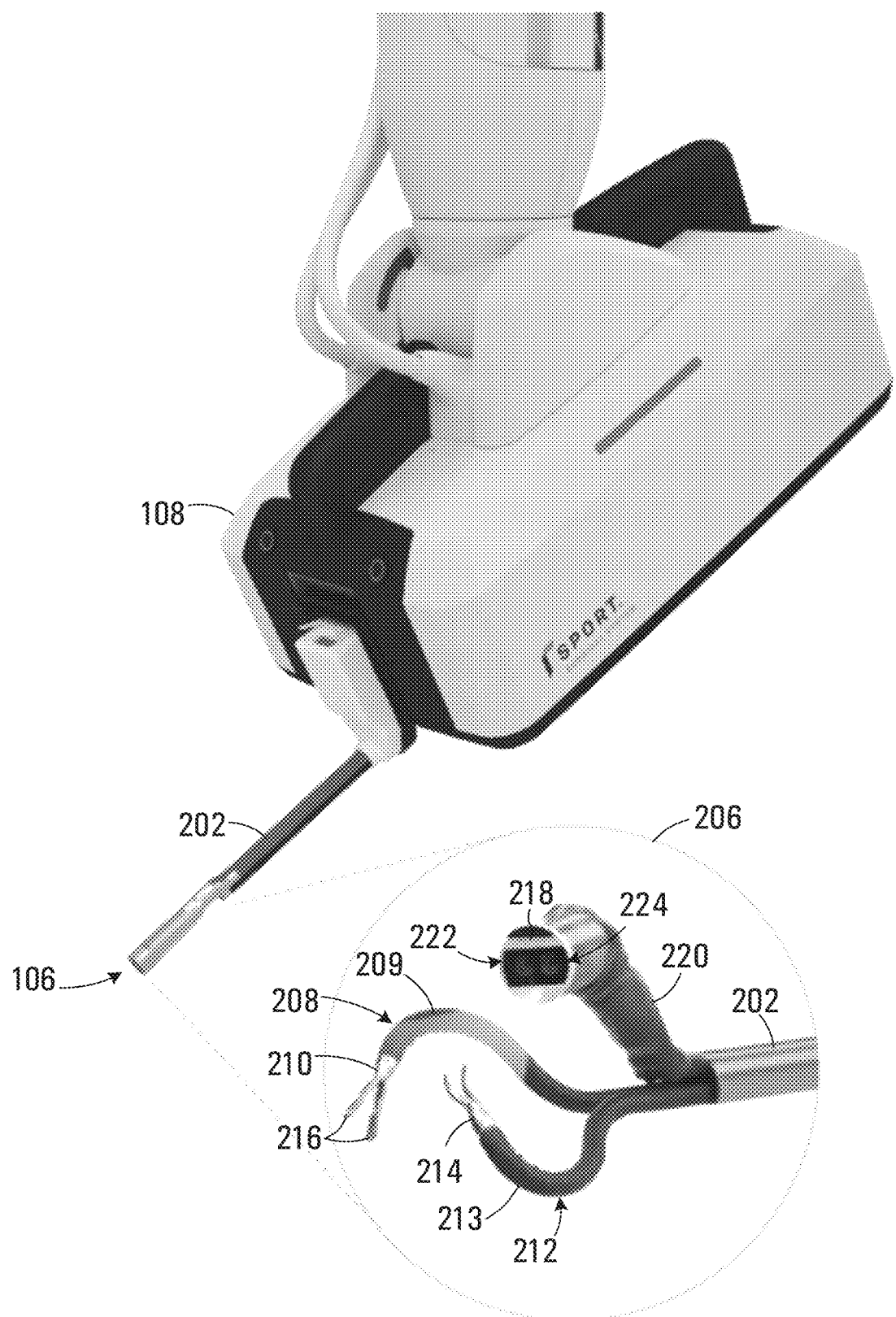
FIG. 2 is a perspective view of an instrument mount of the robotic surgery system shown in FIG. 1.

The instrument 106 and instrument mount 108 are shown in more detail in FIG. 2. Referring to FIG. 2 the instrument 106 includes an insertion tube 202 that is inserted through an incision in a wall of the patient's abdomen or other body cavity to provide access to a surgical workspace within the body cavity. Once inserted into the surgical workspace, the instrument 106 is deployed as shown in the insert 206 in FIG. 2. In this embodiment the instrument 106 includes a right side instrument 208 comprising a positioning device 209 and an end effector 210 and a left side instrument 212 comprising a positioning device 213 and an end effector 214.

In the embodiment shown the end effector 210 is a pair of forceps having opposing moveable gripper jaws 216 controlled by the instrument drive for grasping tissue, while the end effector 214 is a pair of curved dissecting forceps. The instrument 106 also includes a camera 218 deployed on an articulated arm 220 that is able to pan and tilt the camera. The camera 218 includes a pair of spaced apart image sensors 222 and 224 for producing stereoscopic views of the surgical workspace. The instruments 208 and 212 and the camera 218 are initially positioned in-line with the insertion tube 202 prior to insertion through the incision and then deployed as shown at 206.

Referring back to FIG. 1, the input device 110 includes a right input device 116 and a left input device 118. The right input device 116 includes a right hand controller 112 and the left input device 118 includes a left hand controller 114, the hand controllers being mechanically coupled to the respective input devices. The workstation 102 also includes a workstation processor circuit 120, which is in communication with the input devices 116 and 118 and the hand controllers 112 and 114 for receiving input from a surgeon. The instrument cart 104 also includes an instrument processor circuit 130 for controlling the instrument 106. In this embodiment the instrument processor circuit 130 is in communication with the workstation processor circuit 120 via an interface cable 132 for transmitting signals between the workstation processor circuit 120 and the instrument processor circuit 130. In other embodiments communication between the workstation processor circuit 120 and the processor circuit 130 may be wireless or via a computer network, and the workstation 102 and may even be located remotely from the instrument cart 104.

The workstation 102 also includes a display 122 in communication with the workstation processor circuit 120 for displaying real time images and/or other graphical depictions of the surgical workspace. In this embodiment where the camera 218 includes the pair of spaced apart image sensors 222 and 224, the display 122 is configured to provide separate 2D stereoscopic views of the surgical workspace that provide a 3D depth effect when viewed through suitable stereoscopic spectacles worn by the surgeon.

The workstation 102 also includes a footswitch 134, which is actuable by the surgeon to provide an enablement signal to the workstation processor circuit 120. The enablement signal has an active state and an inactive state and in this embodiment depressing the footswitch 134 causes the enablement signal to change from the active state to the inactive state. The active state of the enablement signal permits movement of the instrument 106 in response to the input signals produced by the input device 110 while the inactive state inhibits movement of the instrument.

The input signals are generated by the right and left input devices 116 and 118 in response to movement of the hand controllers 112 and 114 by a surgeon within an input device workspace. The positioning devices 209 and 213 associated with the instruments 208 and 212 spatially position the respective end effectors 210 and 214 in the surgical workspace in response to the input signals.

Figure 3:
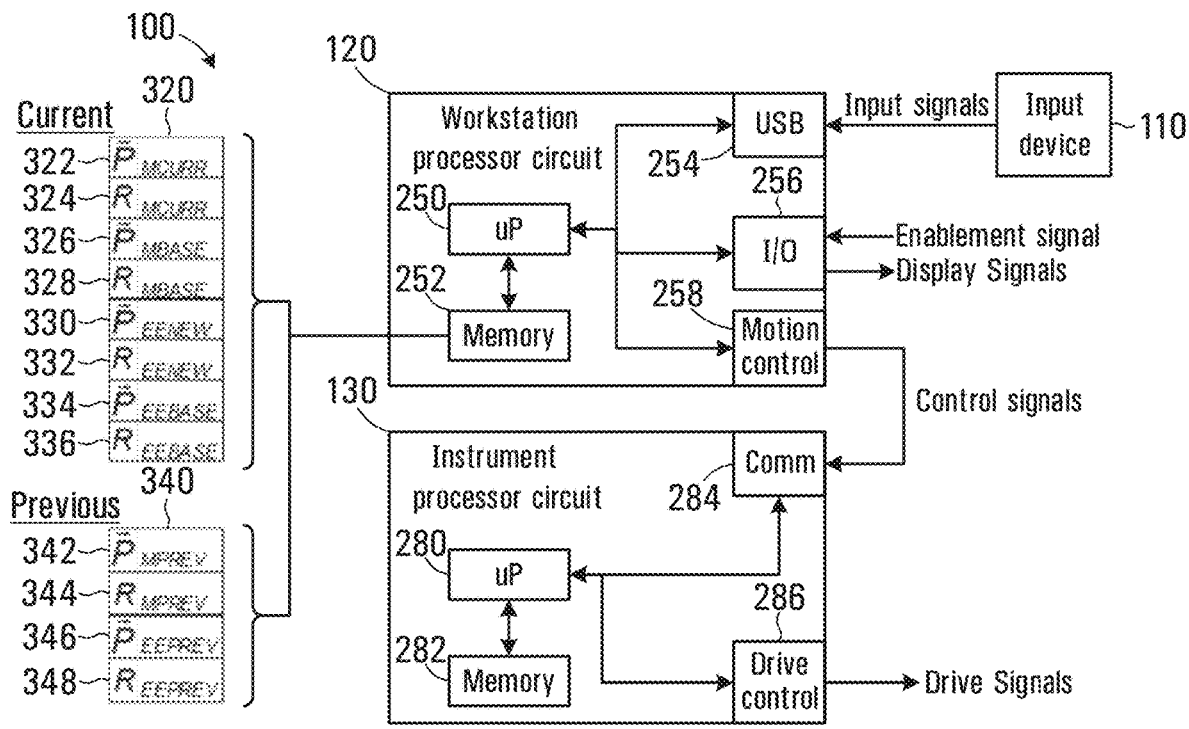
FIG. 3 is a block diagram of the processor circuit elements of the robotic surgery system shown in FIG. 1.

A block diagram of the processor circuit elements of the system 100 is shown in FIG. 3. Referring to FIG. 3 the workstation processor circuit 120 includes a microprocessor 250. The workstation processor circuit 120 also includes a workstation memory 252, a USB interface 254, an input/output 256 and a motion control interface 258, all of which are in communication with the microprocessor 250. The input/output 256 includes an input for receiving an enablement signal from the footswitch 134 and an output for producing display signals for driving the display 122.

In this embodiment the input device 110 communicates using a USB protocol and the USB interface 254 receives input signals produced by the input device in response to movements of the hand controllers 112 and 114. The microprocessor 250 processes the input signals based on a current mapping between the input device workspace and the surgical workspace and causes the motion control interface 258 to transmit control signals, which are conveyed to the instrument processor circuit 130 via the interface cable 132. The mapping may include a scale factor that scales movements in input device workspace to produce scaled movements in surgical workspace. For example a 100 mm translation in input device workspace may be scaled by a scale factor of 0.5 to produce a 50 mm movement in surgical workspace for fine movement.

The enablement signal produced by the footswitch 134 is received at the input/output 256. The workstation memory 252 includes a current buffer 320 and a previous buffer 340 including a plurality of stores for storing values associated with the control signals, as described later herein.

The instrument processor circuit 130 includes a microprocessor 280, a memory 282, a communications interface 284, and a drive control interface 286, all of which are in communication with the microprocessor. The microprocessor 280 receives the input signals at the communications interface 284. The microprocessor 280 processes the control signals and causes the drive control interface 286 to produce drive signals for moving the instruments 208 and 212.

The workstation processor circuit 120 thus acts as a master subsystem for receiving user input, while the instrument processor circuit 130 and instruments 208 and 212 act as a slave subsystem in responding to the user input.

Figure 4:
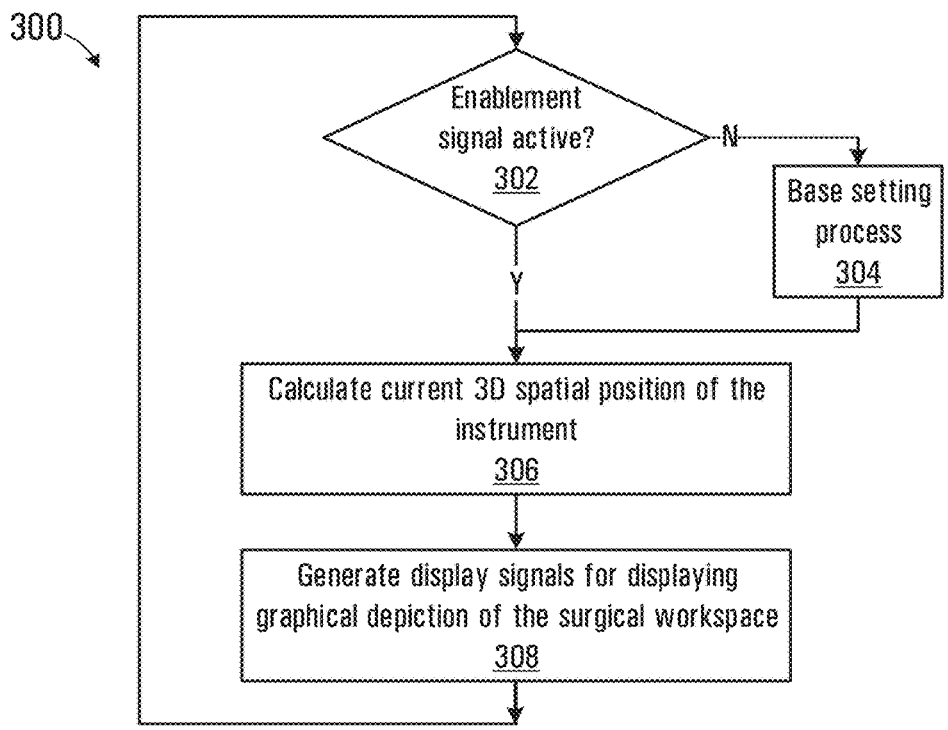
FIG. 4 is a flowchart depicting blocks of code for directing a workstation processor circuit shown in FIG. 3 to display a representation of a spatial position of an instrument.

Referring to FIG. 4, a flowchart depicting blocks of code for directing the workstation processor circuit 120 to display a representation of a spatial position of the instrument 106 is shown generally at 300. The blocks generally represent codes that direct the microprocessor 250 to perform various functions. The actual code to implement each block may be written in any suitable program language, such as C, C++, C#, Java, OpenGL, and/or assembly code, for example.

The process 300 begins at block 302, which directs the microprocessor 250 to determine whether the enablement signal is active. If the footswitch 134 is not currently being depressed then the instruments 208 and 212 are under control of the input device 110 and block 302 directs the microprocessor 250 to block 306. If the footswitch 134 is currently depressed then movement of the instrument 106 is inhibited and block 302 directs the microprocessor 250 to block 304 to execute a base setting process, which will be described later herein. Following the base setting process at block 304, the microprocessor 250 is directed to block 306.

Block 306 directs the microprocessor 250 to calculate a current three-dimensional (3D) spatial position of the instruments 208 and 212 within the surgical workspace for current input signals received from the input device 110. Referring back to FIG. 2, the right side positioning device 209 and left side positioning device 213 of the instruments 208 and 212 are shown actuated to each assume a posture in accordance with the control signals received at the instrument processor circuit 130. Similarly the end effectors 210 and 214 are disposed in a posture in accordance with the control signals received at the instrument processor circuit 130. The 3D spatial position of the instruments 208 and 212 herein refers to 3D positions of each portion of instruments including the positioning devices 209 and 213 and the end effectors 210 and 214. Details of the calculation of these 3D positions in surgical workspace are described later herein.

Block 308 then directs the microprocessor 250 to generate display signals for displaying a graphical depiction of the surgical workspace on the display 122. Referring back to FIG. 1, a right graphical depiction 136 is displayed on the display 122 for the right side instrument 208. Similarly, a left graphical depiction 138 is displayed for the left side instrument 212. The graphical depictions 136 and 138 are displayed at a peripheral region of the display 122 to prevent obscuring a live view 140 of the surgical workspace also displayed on the display.

Block 308 then directs the microprocessor 250 back to block 302 and the process 300 is repeated. In one embodiment the process 300 is repeated at a frequency of about 1 kHz.

Figure 5:
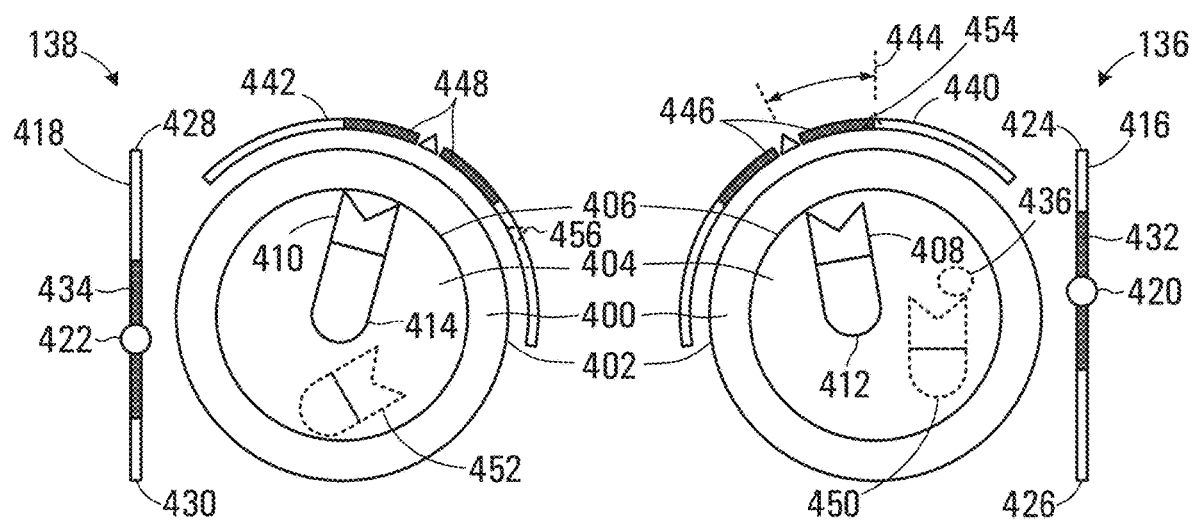
FIG. 5 is a schematic view of graphical depictions generated by the workstation processor circuit shown in FIG. 3.

Referring to FIG. 5, the graphical depictions 136 and 138 are shown in larger scale in FIG. 5. The graphical depictions 136 and 138 are presented as a planar representation including a positioning device movement region 400 having a boundary 402 indicating limitations to transverse movements (translation and orientation) of the positioning device 209 within the surgical workspace. The graphical depictions 136 and 138 also include an end effector movement region 404 having a boundary 406 representing a further region within which the end effector 210 is able to move. Even when the positioning device 209 is at the boundary 402, the end effector 210 may still be able to turn outwardly to access the end effector movement region 404 beyond the positioning device movement region 400.

The graphical depictions 136 and 138 also include a two-dimensional (2D) projection of the current spatial position of the respective positioning devices 209 and 213 and the end effectors 210 and 214. In the embodiment shown the end effectors 210 and 214 are represented by indicators 408 and 410 that indicate at least an approximate orientation of jaws of the respective end effectors. The positioning devices 209 and 213 are represented by areas 412 and 414 corresponding to 2D projected extents of portions of the positioning devices onto the planar representation.

The graphical depictions 136 and 138 also each include an instrument depth range 416 and 418 indicating limitations to axial movement of the instruments into the surgical workspace. The limitations to axial movement of the instrument are represented by ends 424 and 426 of the instrument depth range 416 and ends 428 and 430 of the instrument depth range 418. The instrument depth ranges 416 and 418 also each include a current depth indicator 420 and 422 (in this case a circle) representing a current depth of the end effector within the respective instrument depth ranges. The current depth indicator 420 is closer to the end 424 of the range 416 than the current depth indicator 422, since the right side instrument 208 is located further into the surgical workspace than the left side instrument 212 (as shown in FIG. 2). The instrument depth range 416 also includes an input device depth range 432 (shown as a hatched area) representing a portion of the instrument depth range 416 that is accessible for a current mapping between the input device workspace and the surgical workspace. Similarly, the instrument depth range 418 includes an input device depth range 434 (shown as a hatched area) representing a portion of the instrument depth range 418 that is accessible for a current mapping between the input device workspace and the surgical workspace.

The input signals produced by the input device 110 also include rotation signals defining a current rotation of each of the hand controllers 112 and 114. The rotation signals are used by the workstation processor circuit 120 to produce control signals for causing rotation of the respective end effectors 210 and 214 in the surgical workspace. The graphical depictions 136 and 138 shown in FIG. 5 also include instrument rotation ranges 440 and 442 indicating limitations on rotational movements of the end effectors 210 and 214. In the graphical depictions 136 and 138 a "Δ" indicator represents a current rotation of the end effectors 210 and 214 with respect to a reference, which in FIG. 5 is taken as a vertical line 444 (shown only for the right graphical depiction 136 in FIG. 5). The graphical depictions 136 and 138 further display input device rotation ranges 446 and 448 (shown as hatched areas) representing a portion of the respective instrument rotation ranges 440 and 442 that are accessible for a current mapping between the input device workspace and the surgical workspace.

As disclosed above, blocks 302-308 of the process 300 are repeated at a frequency of about 1 kHz, thus updating the graphical depictions 136 and 138 to provide the surgeon with a near real-time display of the spatial position of the instruments 208 and 212. In the embodiment shown in FIG. 1-4 the instrument 106 includes a pair of instruments 208 and 212, however in other embodiments the system 100 may have a single instrument and only a single graphical depiction would thus be displayed. Alternatively, where more than two instruments are used, a graphical depiction may be displayed for each instrument.

Figure 6:
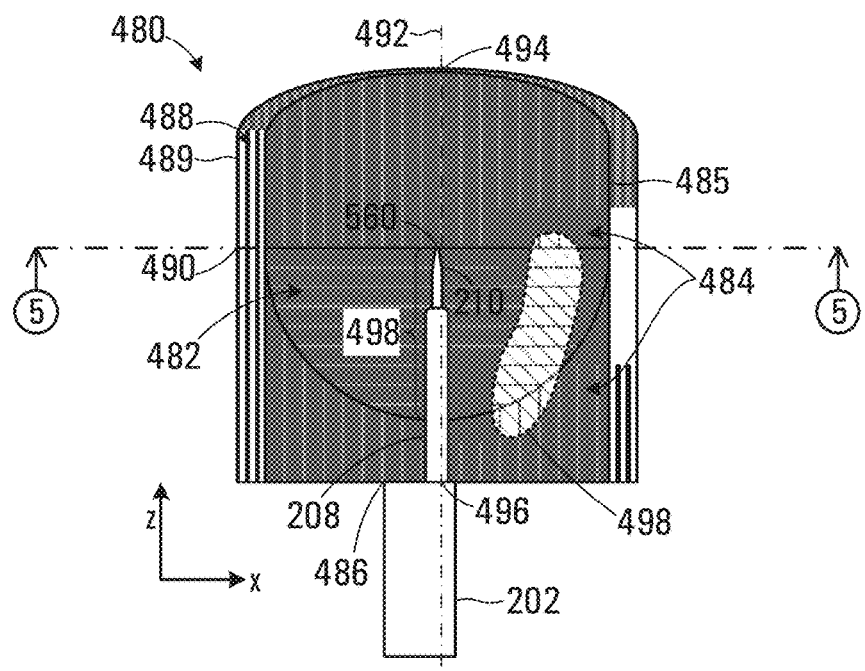
FIG. 6 is a schematic representation of a surgical workspace and an input device workspace for a right side instrument of the robotic surgery system shown in FIG. 1.

Referring to FIG. 6, a schematic representation of the surgical workspace and the input device workspace for the right side instrument 208 as viewed from above the input device 116 is shown at 480. The hand controller 112 of the input device 116 is moveable within a hemispherical 3D volume and the corresponding input device workspace is shown in FIG. 6 as a horizontally hatched semi-circular area 482. In FIG. 6, the input device workspace 482 is shown superimposed on the surgical workspace 484, which is represented by vertically hatched areas accessible by the right side instrument 208. The surgical workspace 484 is also a 3D volume and has a boundary surface 485 defining constraints to movement of the positioning device 209. A point 486 represents a point of insertion of the insertion tube 202 through the wall of the patient's body cavity.

The boundary surface 485 in FIG. 6 and the planar representation of the boundary 402 in FIG. 5 represent limitations to movement of the instrument 208 and end effector 210 based on the extent of the input device workspace 482 within the surgical workspace 484. Additional limitations may be placed on movement of the instrument 208 and end effector 210 due to the patient's anatomy. For example, portions of other organs, vasculature, and other sensitive tissues may also limit movement of the instrument 208 and end effector 210 within the surgical workspace 484. In another embodiment, one or more keep-out zones 498 may be designated within the surgical workspace 484 and the boundary surface 485 may be generated to include these keep-out zones. The keep-out zones 498 are used to further limit movement of the instrument 208 and end effector 210 within the input device workspace 482. Designation of the keep-out zones 498 may be in accordance with input from the surgeon, which may be received at the input device 110. Alternatively, the keep out zones 498 may be designated in accordance with imaging or other patient data that is uploaded to the workstation processor circuit 120. For example, if the patient has had imaging such as magnetic resonance imaging (MRI) or a CT scan, patient specific data relating to the surgical site may be used to define the one or more keep-out zones 498. Subsequently when generating the graphical depictions 136 and 138, the keep-out zones 498 would be included in the definitions of the boundary 402 as an additional zone 436 within the boundary.

Movements of the hand controller 112 of the input device 116 are able to cause the positioning device 209 of the instrument 208 to move within the surgical workspace 484 while the end effector 210 is capable of extending outwardly to reach into a region 488 for the current mapping. The area 488 represents an additional portion of surgical workspace that can be accessed by the end effector 210 and has a 3D boundary surface 489.

The right graphical depiction 136 shown in FIG. 5 generally corresponds to a transverse cross-section taken along the line 5-5, where the intersection of the line 5-5 defines the boundary 402 of the positioning device movement region 400 and the boundary 406 of the end effector movement region 404 as shown in FIG. 5. The representation in FIG. 6 is shown for the right input device 116 and right hand controller 112 controlling the right side instrument 208. The left input device 118, left hand controller 114, and left side instrument 212 have been omitted for sake of clarity but may be similarly represented.

Changes in the mapping between the input signals produced by the input device 110 and the control signals produced by the workstation processor circuit 120 at the motion control interface 258 may be made when the foot-switch 134 is depressed allowing the hand controllers 112 and 114 to be repositioned to access a different portion of the surgical workspace 484 or in response to a change of scale factor, allowing a larger or smaller proportion of the surgical workspace to be accessed.

Input Device

Figure 7:
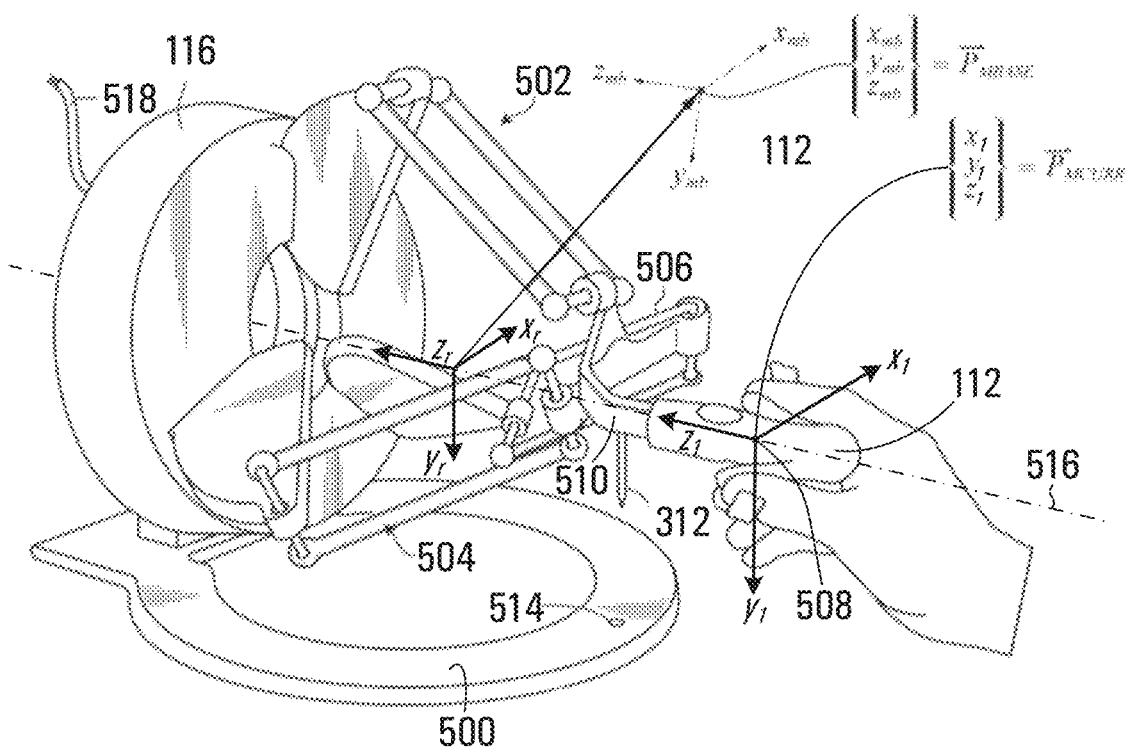
FIG. 7 is a perspective view of a right input device of the robotic surgery system shown in FIG. 1.

The right input device 116 is shown in greater detail in FIG. 7. For simplicity, only the right input device 116 will be further described, it being understood that left input device 118 operates in the same way. Referring to FIG. 7, the input device 116 is supported on a base 500 and includes arms 502, 504, and 506. The right hand controller 112 is mounted to the arms 502-506 to permit positioning and rotation about orthogonal axes $x_1$, $y_1$ and $z_1$ of a Cartesian reference frame. The Cartesian reference frame has an origin at a point midway along a body of the hand controller 112 and the location of the origin defines the hand controller position 508 (i.e. at the origin). In this embodiment, the hand controller 112 is mounted on a gimbal mount 510. The arms 502-506 confine movements of the hand controller 112 and hence the hand controller position 508 to within the hemispherical input device workspace, as shown in FIG. 6. In one embodiment the input device 116 may also be configured to generate haptic forces for providing haptic feedback to the hand controller 112 through the arms 502-506.

The input device 116 has sensors (not shown) that sense the position of each of the arms 502-506 and rotation of the hand controller 112 about each of the $x_1$, $y_1$ and $z_1$ axes and produces signals representing the position of the hand controller in the workspace and the rotational orientation of hand controller relative to an input device Cartesian reference frame $x_r$, $y_r$, $z_r$. In this embodiment, the position and orientation signals are transmitted as input signals via a USB connection 518 to the USB interface 254 of the workstation processor circuit 120.

In this embodiment, the gimbal mount 510 has a pin 512 extending downwardly from the mount and the base 500 includes a calibration opening 514 for receiving the pin. When the pin 512 is received in the opening 514 the input device 116 is located in a calibration position that is defined relative to the input device Cartesian reference frame $x_r$, $y_r$, $z_r$. The input device reference frame has an $x_r$-$z_r$ plane parallel to the base 500 and a $y_r$ axis perpendicular to the base. The $z_r$ axis is parallel to the base 500 and is coincident with an axis 516 passing centrally through the input device 116.

The input device 116 produces current hand controller signals and current hand controller orientation signals that represent the current position and orientation of the hand controller 112. The signals may be represented by a current hand controller position vector and a current hand controller rotation matrix. The current hand controller position vector is given by:

$$\vec{P}_{MCURR} = \begin{Bmatrix} x_1 \\ y_1 \\ z_1 \end{Bmatrix},$$

where $x_1$, $y_1$, and $z_1$ represent coordinates of the hand controller position 508 (i.e. the origin of the coordinate system $x_1$, $y_1$, $z_1$) relative to the input device reference frame $x_r$, $y_r$, $z_r$. The current hand controller rotation matrix is given by:

$$R_{MCURR} = \begin{bmatrix} x_{1x} & y_{1x} & z_{1x} \\ x_{1y} & y_{1y} & z_{1y} \\ x_{1z} & y_{1z} & z_{1z} \end{bmatrix},$$

where the columns of the matrix represent the axes of the hand controller reference frame $x_1$, $y_1$, $z_1$ relative to the input device reference frame $x_r$, $y_r$, $z_r$. The matrix $R_{MCURR}$ thus defines the current rotational orientation of the hand controller 112 relative to the $x_r$, $y_r$, and $z_r$ fixed master reference frame. The current hand controller position vector $\vec{P}_{MCURR}$ and current handle rotation matrix $R_{MCURR}$ are transmitted as current hand controller position and current hand controller orientation signals via the USB connection 518 to the USB interface 254 of the workstation processor circuit 120. The workstation processor circuit 120 stores the three values representing the current handle position vector $\vec{P}_{MCURR}$ in a store 322 and the nine values representing the current hand controller rotation matrix $R_{MCURR}$ in a store 324 of the current buffer 320 of workstation memory 252.

Instrument

Figure 8:
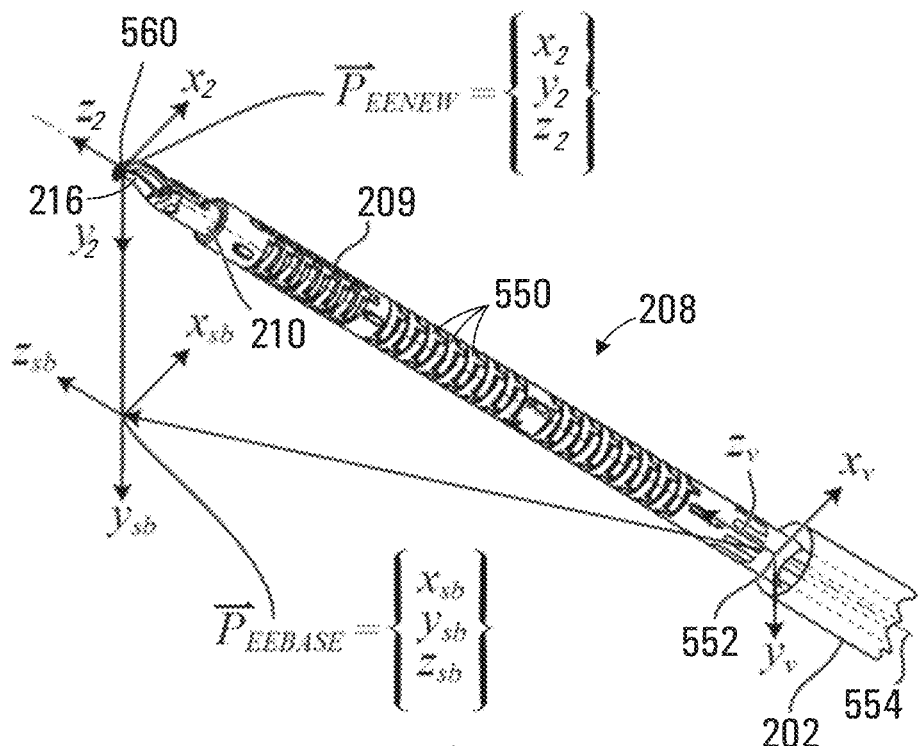
FIG. 8 is a perspective view of the right side instrument of the robotic surgery system shown in FIG. 1.

The right side instrument 208 is shown in greater detail in FIG. 8. Referring to FIG. 8, the positioning device 209 is configured to position the end effector 210 within the surgical workspace by activating various drivers in the instrument mount 108 in response to the drive signals produced by the drive control interface 286 of the instrument processor circuit 130 in response to the control signals received at the communications interface 284 from the workstation processor circuit 120. The drive signals are produced based on the current hand controller position vector $\vec{P}_{MCURR}$ and current hand controller rotation matrix $R_{MCURR}$ are stored in the stores 322 and 324 of the current buffer 320 in the workstation memory 252.

The instrument 208 includes a plurality of the identical "vertebra" 550 as described in U.S. Patent Publication No. 2016/0143633, which is incorporated herein by reference. The vertebra 550 are operable to move with respect to each other when control wires passing through the vertebra are extended or retracted to cause movements of the positioning device 209. The position and orientation of the end effector 210 is defined relative to a fixed slave reference frame having axes $x_v$, $y_v$ and $z_v$, which intersect at a point referred to as the fixed slave reference position 552. The fixed slave reference position 552 lies on a longitudinal axis 554 of the instrument 208 and is contained in a plane perpendicular to the longitudinal axis and containing a distal edge of the insertion tube 202.

In the embodiment shown, the end effector 210 includes gripper jaws 216, which may be positioned and oriented within an end effector workspace. A tip of the gripper jaws 216 may be designated as an end effector position 560 defined as the origin of an end effector Cartesian reference frame $x_2$, $y_2$, $z_2$. The end effector position 560 is defined relative to the slave reference position 552 and the end effector may be positioned and orientated relative to the fixed slave reference frame $x_v$, $y_v$, $z_v$, for causing movement of the positioning device 209 and/or the end effector 210.

The current hand controller position signal $\vec{P}_{MCURR}$ and current hand controller orientation signal $R_{MCURR}$ cause movement of the end effector 210 of the instrument 208 to new end effector positions and desired new end effector orientations and are represented by a new end effector position vector $\vec{P}_{EENEW}$:

$$P_{EENEW} = \begin{Bmatrix} x_2 \\ y_2 \\ z_2 \end{Bmatrix},$$

where $x_2$, $y_2$, and $z_2$ represent coordinates of the end effector position 560 within the end effector workspace relative to the $x_v$, $y_v$, $z_v$ fixed slave reference frame, and a 3×3 end effector rotation matrix $R_{EENEW}$:

$$R_{EENEW} = \begin{bmatrix} x_{2x} & y_{2x} & z_{2x} \\ x_{2y} & y_{2y} & z_{2y} \\ x_{2z} & y_{2z} & z_{2z} \end{bmatrix},$$

where the columns of the $R_{EENEW}$ matrix represent the axes of the end effector reference frame $x_2$, $y_2$, and $z_2$ written in the fixed slave reference frame $x_v$, $y_v$, and $z_v$. $R_{EENEW}$ thus defines a new orientation of the end effector 210 in the end effector workspace, relative to the $x_v$, $y_v$, and $z_v$ fixed slave reference frame. Values for the vector $\vec{P}_{EENEW}$ and rotation matrix $R_{EENEW}$ are calculated as described later herein and stored in stores 330 and 332 of the current buffer 320 of the workstation memory 252 respectively.

Base Setting Process

When the system 100 initially starts up, the workstation processor circuit 120 sets a master base position vector $\vec{P}_{MBASE}$ equal to the current hand controller vector $\vec{P}_{MCURR}$ and causes a definable master base rotation matrix $R_{MBASE}$ to define an orientation that is the same as the current orientation defined by the hand controller rotation matrix $R_{MCURR}$ associated with the current hand controller rotation. At startup the following operations are therefore performed:

$$\vec{P}_{MBASE} = \vec{P}_{MCURR}, \text{ and}$$

$$R_{MBASE} = R_{MCURR}.$$

The hand controller 112 reference frame represented by the axes $x_1$, $y_1$, and $z_1$ shown in FIG. 7 and the definable master base reference frame represented by the axes $x_{mb}$, $y_{mb}$, and $z_{mb}$ (also shown in FIG. 7) thus coincide at startup of the system 100. Referring back to FIG. 3, the workstation processor circuit 120 stores the values representing the definable master base position vector $\vec{P}_{MBASE}$ and the definable master base rotation matrix $R_{MBASE}$ in the stores 326 and 328 of the current buffer 320 of the workstation memory 252.

At startup of the system 100 there would be no previously stored values for the new end effector position vector $\vec{P}_{EENEW}$ and the new end effector Rotation matrix $R_{EENEW}$ and in one embodiment these values are set to home configuration values. A home configuration may be defined that produces a generally straight positioning device 209 of the instrument 208 as shown in FIG. 8 and the values of $\vec{P}_{EENEW}$ and $R_{EENEW}$ for the home configuration may be preconfigured at initialization. On startup of the system 100 the workstation processor circuit 120 also causes a definable end effector base position vector $\vec{P}_{EEBASE}$ and a definable end effector base rotation matrix $R_{EEBASE}$ to be set to the home configuration values of $\vec{P}_{EENEW}$ and $R_{EENEW}$. In other embodiments, the home configuration may define configuration variables to produce different bent or both straight and bent instrument positioning device poses for the home configuration. At startup the following operations are therefore performed:

$$\vec{P}_{EEBASE} = \vec{P}_{EENEW}, \text{ and}$$

$$R_{EEBASE} = R_{EENEW}.$$

The end effector reference frame represented by the axes $x_2$, $y_2$, and $z_2$ shown in FIG. 8 and the definable slave base reference frame represented by the axes $x_{sb}$, $y_{sb}$, and $z_{sb}$ thus coincide at startup of the system 100. Referring back to FIG. 3, the workstation processor circuit 120 stores the values $x_{sb}$, $y_{sb}$, and $z_{sb}$ representing the definable slave base position vector $\vec{P}_{EEBASE}$ in store 334 and stores the values representing the definable slave base rotation matrix $R_{MBASE}$ in a store 336 of the current buffer 320 of the workstation memory 252.

Figure 9:
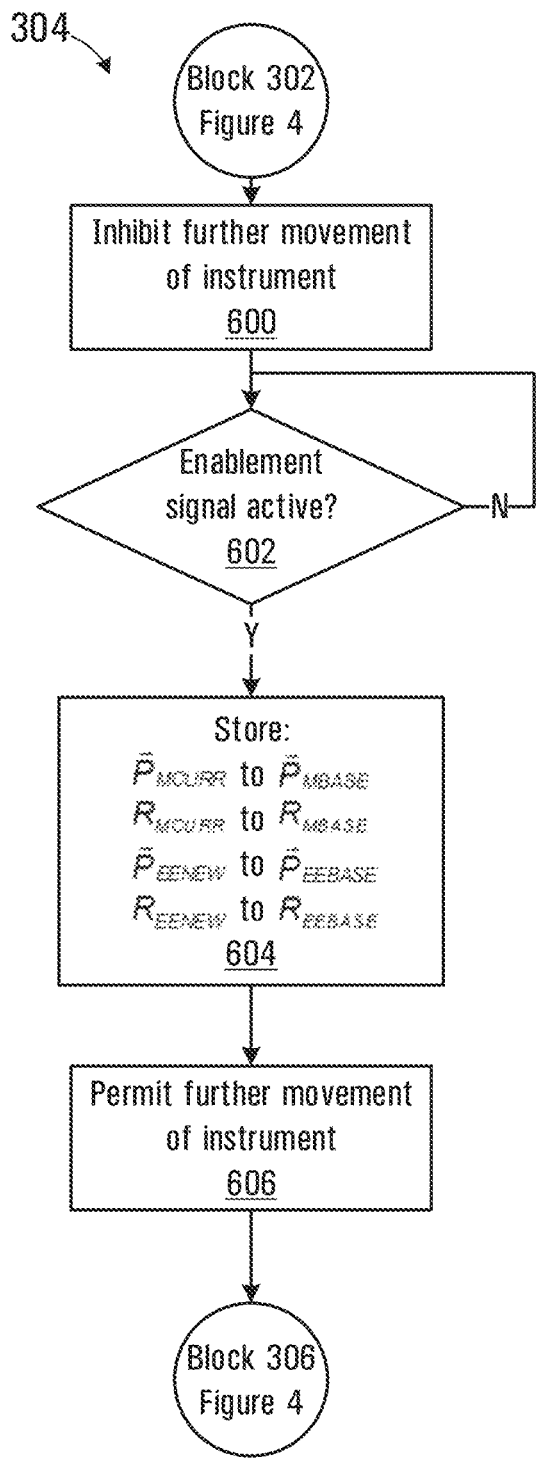
FIG. 9 is a flowchart depicting blocks of code for directing the workstation processor circuit shown in FIG. 3 to execute a base setting process.

The base setting process (block 304 of the process 300 shown in FIG. 4) is executed asynchronously when the enablement signal produced by the footswitch 134 transitions from the active state to the inactive state at block 302. Further details of the base setting process 304 are shown as a process flowchart in FIG. 9. The base setting process 304 begins at block 600, which directs the microprocessor 250 of the workstation processor circuit 120 to inhibit further movement of the instrument 208 by transmitting control signals via the motion control interface 258 that cause the instrument processor circuit 130 to produce drive signals at the drive control interface 286 that do not to cause further movements of the instrument 208. In one embodiment the microprocessor 250 maintains the same control signals and since the drive signals produced by the drive control interface 286 are produced in response to the control signals, the drive signals will also be maintained at the values that were active at the time the footswitch 134 was depressed. The instrument 208 will thus remain immobile at a current position and orientation.

Block 602 then directs the microprocessor 250 to determine whether the enablement signal has transitioned from the inactive state to the active state again. If the enablement signal remains in the inactive state, block 602 directs the microprocessor 250 to repeat block 602 and the process 304 is thus effectively suspended while the enablement signal is in the inactive state. When the enablement signal transitions from the inactive state to the active state, block 602 directs the microprocessor 250 to block 604.

Block 604 directs the microprocessor 250 to set new base positions and orientations for the hand controller 112 and end effector 210 respectively. While the footswitch 134 is depressed the surgeon may move the hand controller 112 to a new location to relocate the input device workspace relative to the surgical workspace. When the enablement signal transitions to the active state, block 604 directs the microprocessor 250 to cause current values of current hand controller position vector $\vec{P}_{MCURR}$ and the hand controller rotation matrix $R_{MCURR}$ to be stored in locations 326 and 328 of the current buffer 320 workstation memory 252 as new values for the master base position vector $\vec{P}_{MBASE}$ and master base rotation matrix $R_{MBASE}$. Block 604 also directs the microprocessor 250 to cause current values for the end effector position signal $\vec{P}_{EENEW}$ and the end effector orientation signal $R_{EENEW}$ to be stored in stores 334 and 336 of the current buffer 320 as the definable end effector base position vector $\vec{P}_{EEBASE}$ and definable slave base rotation matrix $R_{MBASE}$.

The base setting process 304 then continues at block 606, which directs the microprocessor 250 to permit further movement of the instrument 208 while the enablement signal produced by the 134 remains active.

The base setting process 304 thus allows the instrument 208 to be immobilized by depressing the footswitch 134 while the hand controller 112 of the input device 116 is moved to a new location. When the footswitch 134 is released, control of the instrument 208 resumes at the new position of the hand controller 112. The hand controller 112 may thus be repositioned as desired while the instrument remains immobile, preventing unintended movements that may inflict injury to the patient.

In one embodiment, when the footswitch 134 causes the enablement signal to transition to the inactive state, the indicators 408, 412, 410 and 414 in FIG. 5 representing the positions and orientations of the respective left and right instruments 208 and 212 are immobilized on the graphical depictions 136 and 138 at their current respective positions and additional indicators 450 and 452 representing current input device 110 inputs are displayed. The immobilized indicators 408, 412, 410 and 414 represent the position and orientation of the immobilized instruments 208 and 212 while the additional indicators 450 and 452 represent current positions of the input devices 116 and 118 and hand controllers 112 and 114. Subsequently, when the enablement signal again transitions to the active state, the additional indicators 450 and 452 are deleted or gradually faded out and the indicators 408, 412, 410 and 414 are once again rendered active. Aligning the displayed indicators 408 and 450 and the indicators 410 and 452 prior to releasing the footswitch 134 minimizes the offset between the hand controllers 112 and 114 and the respective instruments 208 and 212. Similarly current hand controller rotation indicators 454 and 456 may be displayed at an offset from the indicator representing a current rotation of the end effectors 210 and 214. Accordingly, while the footswitch 134 is depressed, the user can offset roll, orientation and translation (XYZ). When the footswitch 134 is released the instruments 208 and 212 are re-engaged and the roll and translation offset is fixed.

Instrument Position and Orientation

Figure 10:
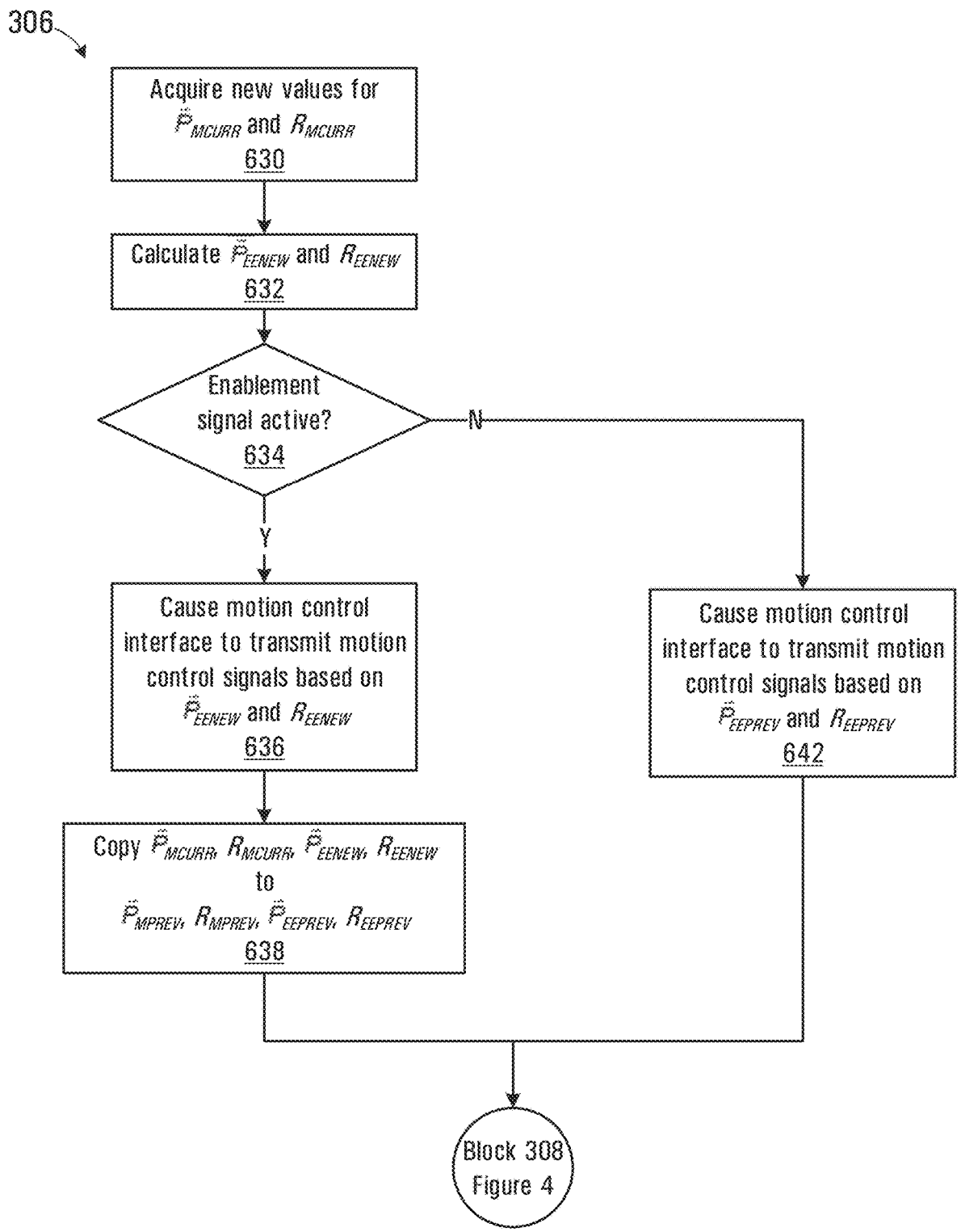
FIG. 10 is a flowchart depicting blocks of code for directing the workstation processor circuit shown in FIG. 3 to execute a process for calculating the 3D spatial position of the instrument.

Further details of block 306 of the process 300 shown in FIG. 3 for calculating the 3D spatial position of the instrument are shown in FIG. 10. Referring to FIG. 10, the process 306 includes blocks of codes executed by the workstation processor circuit 120 for calculating a new end effector position and orientation control signals $\vec{P}_{EENEW}$ and $R_{EENEW}$ in response to the current hand controller position $\vec{P}_{MCURR}$ and hand controller orientation $R_{MCURR}$. These control signals when received by the instrument processor circuit 130 at the communications interface 284 are used by the microprocessor 280 to produce drive signals at the drive control interface 286 to position and orient the end effector 210. In one embodiment the process 306 is executed periodically at a rate of about 1 kHz.

The process 306 begins at block 630 which directs the microprocessor 250 to read current values for $\vec{P}_{MCURR}$ and $R_{MCURR}$ from the current buffer 320 of the workstation memory 252, which represent the current hand controller position vector $\vec{P}_{MCURR}$ and current hand controller matrix $R_{MCURR}$. Block 632 then directs the microprocessor 250 to calculate new end effector position signals $\vec{P}_{EENEW}$ and new end effector orientation signals $R_{EENEW}$ representing a desired end effector position 560 and desired end effector orientation, relative to the fixed slave reference position 552 and the slave base orientation. Block 632 also directs the microprocessor 250 to store values representing the new end effector position vector $\vec{P}_{EENEW}$ in the store 330 and to store values representing the desired end effector orientation matrix $R_{EENEW}$ in the store 332 of the current buffer 320 of the workstation memory 252.

The new end effector position signals $\vec{P}_{EENEW}$ and new end effector orientation signals $R_{EENEW}$ are calculated according to the following relations:

$$\vec{P}_{EENEW} = A(\vec{P}_{MCURR} - \vec{P}_{MBASE}) + \vec{P}_{EEBASE} \qquad \text{Eqn 1a}$$

$$R_{EENEW} = R_{EEBASE} R_{MBASE}^{-1} R_{MCURR} \qquad \text{Eqn 1b}$$

where:

$\vec{P}_{EENEW}$ is the new end effector position vector that represents the new desired position of the end effector 210 in the end effector workspace, and is defined relative to the slave base reference position;

A is a scalar value representing a scaling factor in translational motion between the master and the slave;

$\vec{P}_{MCURR}$ is the current representation of the hand controller position vector stored in the store 322 of the current buffer 320, the hand controller position vector being defined relative to the fixed master reference frame $x_r$, $y_r$, and $z_r$;

$\vec{P}_{MBASE}$ is the last-saved position vector $\vec{P}_{MCURR}$ for the hand controller 112 that was shifted at the last transition of the enablement signal from the inactive state to the active state or on system initialization or by operation of a control interface by an operator;

$\vec{P}_{EEBASE}$ is the last saved position vector $\vec{P}_{EENEW}$ for the end effector 210 that was shifted at the last transition of the enablement signal from the inactive state to the active state or on system initialization;

$R_{EENEW}$ is the new end effector orientation matrix representing the current orientation of the end effector 210, and is defined relative to the fixed slave reference position 552;

$R_{EEBASE}$ is the last-saved rotation matrix $R_{EENEW}$ of the end effector 210 shifted at the last transition of the enablement signal from the inactive state to the active state;

$R_{MBASE}^{-1}$ is the inverse of rotation matrix $R_{MBASE}$, which is the last-saved rotation matrix $R_{MCURR}$ of the hand controller 112 saved at the last transition of the enablement signal from the inactive state to the active state; and $R_{MCURR}$ is the currently acquired rotation matrix representing the orientation of hand controller 112 relative to the fixed master reference frame $x_r$, $y_r$, and $z_r$.

Block 634 then directs the microprocessor 250 to determine whether the enablement signal is in the active state. If the enablement signal is in the active state, block 636 directs the microprocessor 250 to cause the motion control interface 258 to transmit control signals based on the newly calculated values for $\vec{P}_{EENEW}$ and $R_{EENEW}$. When the control signals are received at the communications interface 284 of the instrument processor circuit 130, the microprocessor 280 causes drive signals to be produced to cause the end effector 210 to assume a position and orientation determined by the current position and current orientation of the hand controller 112.

Block 638 then directs the microprocessor 250 to copy the current position vector $\vec{P}_{MCURR}$ and the current rotation matrix $R_{MCURR}$ stored in stores 322 and 324 of the current buffer 320 into stores 342 ($\vec{P}_{MPREV}$) and 344 ($R_{MPREV}$) of the previous buffer 340 of the workstation memory 252. Block 638 also directs the microprocessor 250 to copy the newly calculated end effector position vector $\vec{P}_{EENEW}$ and the newly calculated end effector rotation matrix $R_{EENEW}$ into stores 346 and 348 of the previous buffer 340. By storing the newly calculated end effector position vector $\vec{P}_{EENEW}$ and newly calculated end effector rotation matrix $R_{EENEW}$, as previously calculated end effector position vector $\vec{P}_{EEPREV}$ and previously calculated end effector rotation matrix $R_{EEPREV}$, a subsequently acquired new end effector position vector $\vec{P}_{EENEW}$ and subsequently acquired new end effector rotation matrix $R_{EENEW}$ can be calculated from the next received hand controller position vector $\vec{P}_{MCURR}$ and next receive hand controller rotation matrix $R_{MCURR}$ provided by the input device 116.

If at block 634, the enablement signal is in the inactive state the microprocessor 250 is directed to block 642. Block 642 directs the microprocessor 250 to cause the motion control interface 258 to transmit control signals based on the previously calculated values of $\vec{P}_{EPREV}$ and $R_{EEPREV}$ in the respective stores 346 and 348 of the previous butter 340 of the workstation memory 252. The control signals transmitted by the motion control interface 258 are thus derived from the last saved values of $\vec{P}_{EENEW}$ and $R_{EENEW}$, causing the end effector 210 to remain stationary since the same control signals as previously determined are transmitted to the communications interface 284 of the instrument processor circuit 130. The microprocessor 250 is then directed to block 640.

While enablement signal remains inactive (i.e. while the footswitch 134 is depressed) the control signals transmitted by the motion control interface 258 are based only on the previously calculated end effector position and previously calculated orientation signals $\vec{P}_{EEPREV}$ and $R_{EEPREV}$ that were in effect before the enablement signal transitioned to inactive.

In another embodiment certain special functions may be executed before executing block 636 when the enablement signal is determined to be in the active state at block 634. One example of such a special function is an alignment control function, as described in applicant's co pending U.S. Patent Publication No. 2018/0271607 and U.S. Patent Publication No. 2017/0367777, hereby incorporated by reference in their entirety. For example, in one embodiment an alignment control function may have one of two outcomes. The first outcome may direct the microprocessor 250 to execute block 636, which directs the microprocessor to cause the motion control interface 258 to transmit control signals to the instrument processor circuit 130 based on the newly calculated end effector position and newly calculated end effector orientation $\vec{P}_{EENEW}$ and $R_{EENEW}$. The second outcome directs the microprocessor 250 to execute block 638, which causes the microprocessor to cause the motion control interface 258 to transmit control signals based on a previously calculated end effector position and previously calculated end effector orientation $\vec{P}_{EEPREV}$ and $R_{EEPREV}$. This causes the end effector 210 to assume a position and orientation determined by a previous position and previous orientation of the hand controller 112.

Accordingly, when the enablement signal is in the inactive state, the hand controller 112 can be moved and rotated and the calculations of $\vec{P}_{EENEW}$ and $R_{EENEW}$ will still be performed by block 632, but there will be no movement of the end effector 210, since the previous control signals are sent to the instrument processor circuit 130. This allows "clutching" or repositioning of the hand controller 112 without corresponding movement of the end effector 210. The movement may be useful in relocating the hand controller within the input device workspace to a comfortable position and/or providing an increased range of movement for the end effector 210 within the surgical workspace.

The end effector position vector $\vec{P}_{EENEW}$ or $\vec{P}_{EEPREV}$ and end effector orientation matrix $R_{EENEW}$ or $R_{EEPREV}$ produced at block 636 or block 638 provide a desired location end effector tip 560 with respect to the fixed slave reference position 552. However, in the embodiment shown in FIG. 3, the microprocessor 250 causes the motion control interface 258 to transmit motion control signals that define a pose required by the positioning device 209 to position and orient the end effector 210 in the desired end effector position and orientation. The motion control signals are thus generated based on a kinematic configuration of the positioning device 209 and end effector 210 to position the end effector position 560 at the desired position and orientation.

Motion Control Signals

Figure 11:
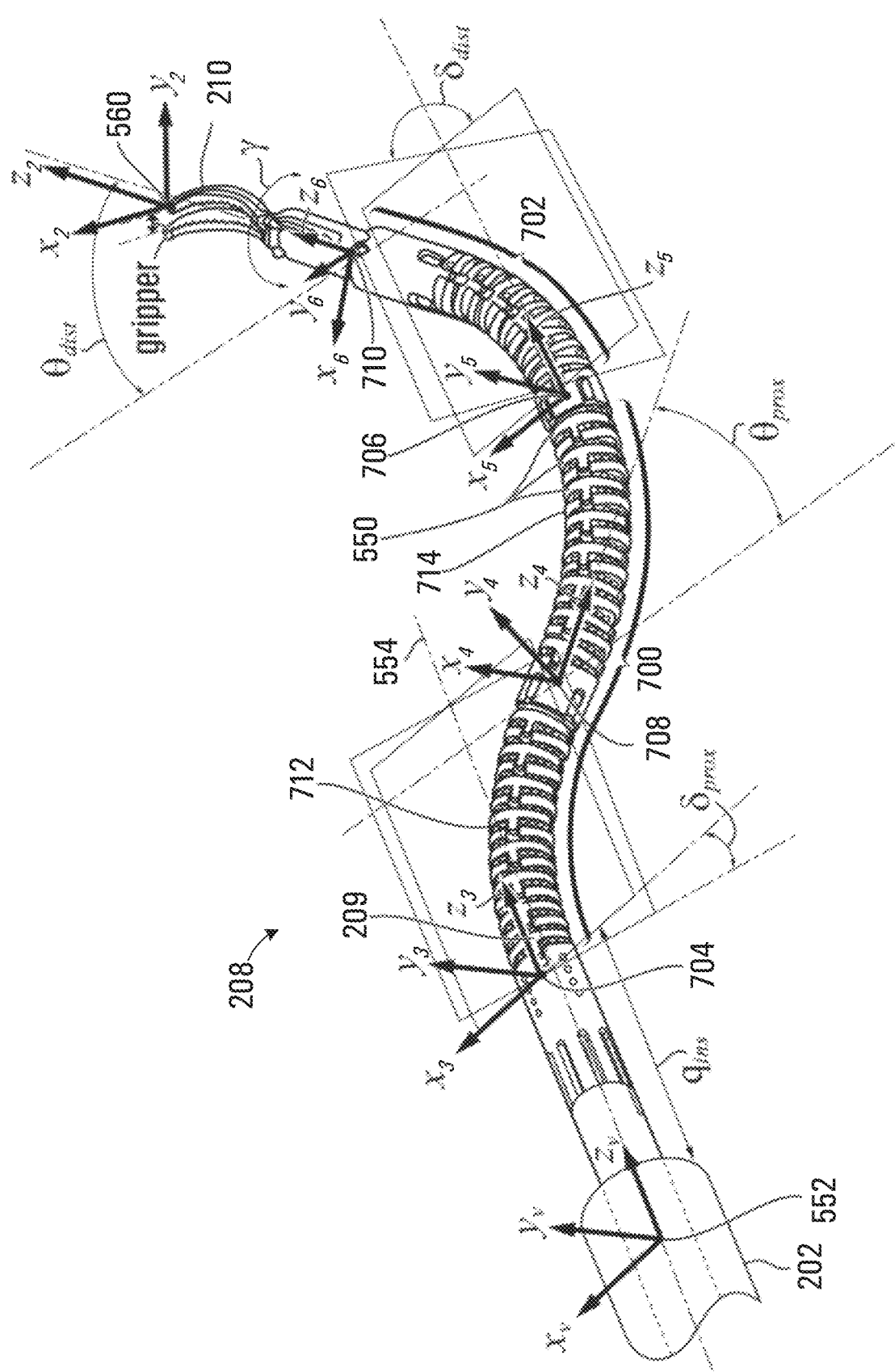
FIG. 11 is a further perspective view of the right side instrument of the robotic surgery system shown in FIG. 1 in a bent condition.
Figure 12:
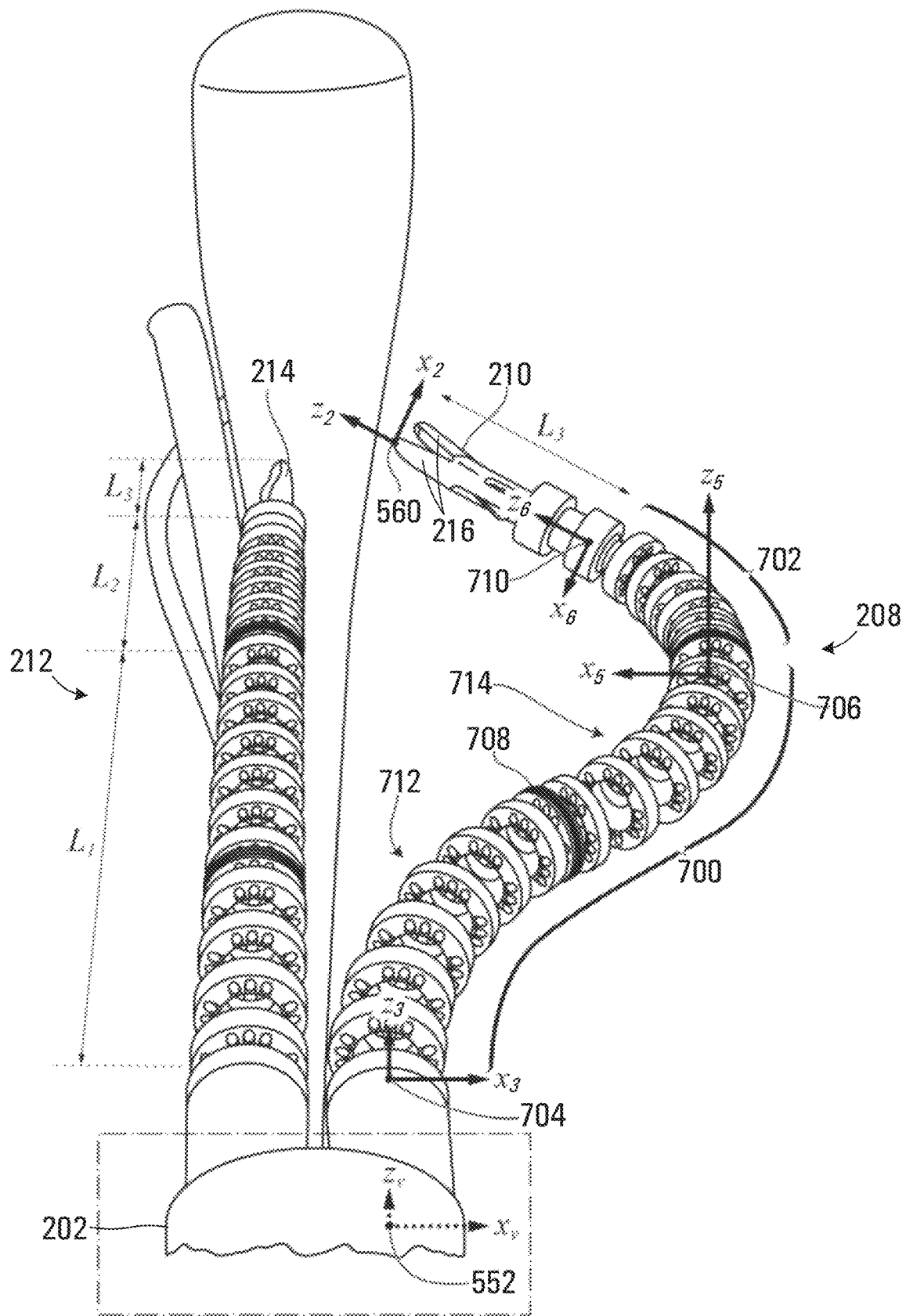
FIG. 12 is a perspective view of the left and right side instruments of the robotic surgery system shown in FIG. 1.

The right side instrument 208 is shown in a bent pose in FIG. 11 and FIG. 12. The left side instrument 212 is also shown in FIG. 12 in a straight pose corresponding to the home configuration. Referring to FIG. 11 and FIG. 12, the positioning device 209 of the instrument 208 has a first articulated segment referred to as an s-segment 700 and a second articulated segment referred to as a distal segment 702. The segments each include a plurality of the vertebra 550. The s-segment 700 begins at a distance from the insertion tube 202, referred to as the insertion distance $q_{ins}$, which is a distance between the fixed slave reference position 552 defined at the origin of the slave fixed base reference frame $x_v$, $y_v$, and $z_v$, and a first position 704 at an origin of a first position reference frame $x_3$, $y_3$, and $z_3$. The insertion distance $q_{ins}$ represents an unbendable portion of the positioning device 209 that extends out of the end of the insertion tube 202. In the embodiment shown, the insertion distance $q_{ins}$ may be about 10-20 mm, while in other embodiments the insertion distance may be longer or shorter, varying from 0-100 mm, for example.

The s-segment 700 extends from the first position 704 to a third position 706 defined as an origin of a third reference frame having axes $x_5$, $y_5$, and $z_5$ and is capable of assuming a smooth s-shape when control wires (not shown) inside the s-segment 700 are pushed and pulled. The s-segment 700 has a mid-point at a second position 708, defined as the origin of a second position reference frame having axes $x_4$, $y_4$, and $z_4$. The s-segment 700 has a length $L_1$, best shown in FIG. 12 for the left side instrument positioning device 213. In the embodiment shown, the length $L_1$ may be about 65 mm.

The distal segment 702 extends from the third position 706 to a fourth position 710 defined as an origin of a fourth reference frame having axes $x_6$, $y_6$, and $z_6$. The distal segment 702 has a length $L_2$, best shown in FIG. 12 for the left side instrument positioning device 213. In the embodiment shown, the length $L_2$ may be about 23 mm.

Each end effector 210 and 214 also has an end effector length, which in the embodiment shown is a gripper length $L_3$ extending from the fourth position 710 to the end effector tip position 560 defined as the origin of the axes $x_2$, $y_2$, and $z_2$. The gripper length $L_3$ is best shown in FIG. 12 again for the left side instrument positioning device 213 and in one embodiment may be about 25 mm. The slave reference position 552, first position 704, second position 708, third position 706, fourth position 710, and the end effector position 560 may collectively be referred to as instrument reference positions.

As described in U.S. Patent Publication No. 2016/0143633 (hereby incorporated herein by reference in its entirety) by pushing and pulling on control wires inside the positioning devices 209 and 213, the s-segments 700 of the positioning devices 209 and 213 may be bent into various degrees of an s-shape, from the straight condition shown in FIG. 8 to a partial s-shape for the right side instrument 208 shown in FIGS. 11 and 12 to a full s-shape. The s-segment 700 is sectional in that it has a first section 712 and a second section 714 on opposite sides of the second position 708. Referring to FIG. 5, the first and second sections 712 and 714 lie in a first bend plane containing the first position 704, second position 708, and third position 706. The first bend plane is at an angle $\delta_{prox}$ to the $x_v$-$z_v$ plane of the fixed slave reference frame $x_v$, $y_v$, and $z_v$. The first section 712 and second section 714 are bent in the first bend plane through opposite but equal angles $\theta_{prox}$ such that no matter the angle $\theta_{prox}$ or the bend plane angle $\delta_{prox}$, the $z_5$ axis of the third position 706 is always parallel to and aligned in the same direction as the $z_v$ axis of the fixed slave reference position 552. Thus, by pushing and pulling on the control wires within the positioning device 209, the third position 706 can be placed at any of a number of discrete positions in space within a cylindrical volume about the first position 704. This cylindrical volume may be referred to as the s-segment workspace.

In addition, the distal segment 702 lies in a second bend plane containing the third position 706 and the fourth position 710. The second bend plane is at an angle $\delta_{dist}$ to the $x_v$-$z_v$ plane of the fixed slave reference frame $x_v$, $y_v$, and $z_v$. The distal segment 702 is bent in the second bend plane at an angle $\vartheta_{dist}$. Thus, by pushing and pulling the control wires within the positioning device 209, the fourth position 710 can be placed within another volume in space about the fourth position 710. This volume may be referred to as the distal workspace. The combination of the s-segment workspace and the distal workspace may be referred to as the positioning device workspace as this represents the total possible movement of the instrument 208 as effected by the positioning device 209. The left side instrument 212 may be similarly positioned by the positioning device 213.

The distance between the fourth position 710 and the end effector position 560 is the distance between the movable portion of the distal segment 702 and the tip of the gripper end effector 210 in the embodiment shown, i.e. the length the gripper length $L_3$ shown in FIG. 12. Generally, a portion of the gripper between the fourth position 710 and the end effector position 560 will be unbendable.

In the embodiment shown, the end effector 210 include moveable gripper jaws 216 that are rotatable about the $z_2$ axis in the $x_2$-$y_2$ plane of the end effector reference frame, the angle of rotation being represented by an angle γ relative to the positive $x_2$ axis. Finally, the gripper jaws 216 may be at any of varying degrees of openness from fully closed to fully open (as limited by a hinge joint of the jaws). The varying degrees of openness may be defined as the "gripper". In summary therefore, the motion control signals are generated based on a kinematic configuration of the positioning device 209 and end effector 210 as defined by the following configuration variables:

$q_{ins}$ represents a distance from the slave reference position 552 defined by axes $x_v$, $y_v$, and $z_v$ to the first position 704 defined by axes $x_3$, $y_3$ and $z_3$ where the s-segment 700 of the positioning device 209 begins;

$\delta_{prox}$ represents a first bend plane in which the s-segment 700 is bent relative to the $x_v$-$y_v$ plane of the fixed slave reference frame;

$\vartheta_{prox}$ represents an angle at which the first and second sections 712 and 714 of the s-segment 700 are bent in the first bend plane;

$\delta_{dist}$ represents a second bend plane in which the distal segment 702 is bent relative to the $x_v$-$y_v$ plane of the fixed slave reference frame;

$\theta_{dist}$ represents an angle through which the distal segment 702 is bent in the second bend plane;

γ represents a rotation of the end effector 210 about axis $z_2$; and

Gripper: represents a degree of openness of the gripper jaws 216 of the end effector 210 (this is a value which is calculated in direct proportion to a signal produced by an actuator (not shown) on the hand controller 112 indicative of an amount of pressure the operator exerts by squeezing the actuator to actuate the jaws 216 to close).

To calculate the configuration variables, it will first be recalled that the end effector rotation matrix $R_{EENEW}$ is a 3×3 matrix:

$$R_{EENEW} = \begin{bmatrix} x_{2x} & y_{2x} & z_{2x} \\ x_{2y} & y_{2y} & z_{2y} \\ x_{2z} & y_{2z} & z_{2z} \end{bmatrix},$$

where the last column of $R_{EENEW}$ is the z-axis of the end effector reference frame written relative to the fixed slave reference frame $x_v$, $y_v$, and $z_v$. The values $\vartheta_{dist}$, $\delta_{dist}$, and γ associated with the distal segment 702 may be calculated according to the relations:

$$\theta_{dist} = \frac{\pi}{2} - a\tan2\left(\sqrt{z_{2x}^2 + z_{2y}^2}, z_{2z}\right) \qquad \text{Eqn 2}$$

$$\delta_{dist} = -a\tan2(z_{2y}, z_{2x}). \qquad \text{Eqn 3}$$

If $|\delta_{dist}| > \frac{\pi}{2}$:

$$\gamma = a\tan2(-y_{2z}, x_{2z}) - \delta_{dist} + \pi \qquad \text{Eqn 4a}$$

else $$\gamma a \tan 2(y_{2z}, -x_{2z}) - \delta_{dist} \qquad \text{Eqn 4b}$$

The third position 706 may then be written in terms of a vector $\bar{p}_{3/v}$ from the fixed slave reference position 552 to the third position. Similarly a vector $\bar{p}_{4/3}$ may be defined from the third position 706 to the fourth position 710 and a vector $\bar{p}_{5/4}$ may be defined from the fourth position 710 to the end effector position 560. These values can then be used to compute the location of third position 706 relative to the fixed slave reference position 552 by subtracting the vectors $\bar{p}_{4/3}$ and $\bar{p}_{5/4}$ from the end effector position vector $\vec{P}_{EENEW}$:

$$\bar{p}_{3/v} = \vec{P}_{EENEW} - \bar{p}_{4/3} - \bar{p}_{5/4} \qquad \text{Eqn 5}$$

where:

$$\bar{p}_{4/3} \cdot \bar{i} = \frac{-L_2 \cos \delta_{dist} (\sin \theta_{dist} - 1)}{\frac{\pi}{2} - \theta_{dist}} \qquad \text{Eqn 6a}$$

$$\bar{p}_{4/3} \cdot \bar{j} = \frac{L_2 \sin \delta_{dist} (\sin \theta_{dist} - 1)}{\frac{\pi}{2} - \theta_{dist}} \qquad \text{Eqn 6b}$$

$$\bar{p}_{4/3} \cdot \bar{k} = \frac{L_2 \cos(\theta_{dist})}{\frac{\pi}{2} - \theta_{dist}} \qquad \text{Eqn 6c}$$

$$\bar{p}_{5/4} \cdot \bar{i} = L_3 \cos(\delta_{dist}) \cos(\theta_{dist}) \qquad \text{Eqn 7a}$$

$$\bar{p}_{5/4} \cdot \bar{j} = -L_3 \sin(\delta_{dist}) \cos(\theta_{dist}) \qquad \text{Eqn 7b}$$

$$\bar{p}_{5/4} \cdot \bar{k} = L_3 \sin(\theta_{dist}), \qquad \text{Eqn 7c}$$

where $\bar{i}$ is a unit vector in the x direction, $\bar{j}$ is a unit vector in the y direction, and $\bar{k}$ is a unit vector in the z direction. The vector $\bar{p}_{3/v}$ from the fixed slave reference position 552 to the third position 706 may then be used to find the configuration variables $\delta_{prox}$ and $\vartheta_{prox}$ for the s-segment 700. The angle $\delta_{prox}$ is calculated by solving the following two equations for $\delta_{prox}$:

$$\bar{p}_{3/v} \cdot \bar{i} = \frac{-L_1 \cos \delta_{prox} (\sin \theta_{prox} - 1)}{\frac{\pi}{2} - \theta_{prox}} \qquad \text{Eqn 8a}$$

$$\bar{p}_{3/v} \cdot \bar{j} = \frac{L_1 \sin \delta_{prox} (\sin \theta_{prox} - 1)}{\frac{\pi}{2} - \theta_{prox}}. \qquad \text{Eqn 8b}$$

Taking a ratio of Eqn 8b and Eqn 8a yields:

$$\delta_{prox} = a \tan 2(-\bar{p}_{3/v} \cdot \bar{j}, \bar{p}_{3/v} \cdot \bar{i}), \qquad \text{Eqn 9}$$

where $\bar{i}$ and $\bar{j}$ are unit vectors in the x and y directions respectively. A closed form solution cannot be found for $\vartheta_{prox}$, and accordingly $\vartheta_{prox}$ must be found using a numerical equation solution to either of equations Eqn 8a or Eqn 8b. For example, a Newton-Raphson method may be employed, which iteratively approximates successively better roots of a real-valued function. The Newton-Raphson method can be implemented using the following equations:

$$f(\theta_{prox}) = \frac{L_1}{\frac{\pi}{2} - \theta_{prox}} \cos \delta_{prox}(1 - \sin \theta_{prox}) - \bar{p}_{3/v} \cdot \bar{i} = 0, \qquad \text{Eqn 10}$$

where $\bar{i}$ is the unit vector in the x direction. The equation Eqn 10 is Eqn 8a rewritten in the form $f(\vartheta_{prox})=0$. The Newton-Raphson method tends to converge very quickly because in the range $0 < \vartheta_{prox} < \pi$ the function has a large radius of curvature and has no local stationary points. Following the Newton-Raphson method, successive improved estimates of $\vartheta_{prox}$ can be made iteratively to satisfy equation Eqn 10 using the following relationship:

$$\theta_{n+1} = \theta_n - \frac{f(\theta_n)}{f'(\theta_n)} \qquad \text{Eqn 11}$$

Finally, upon determination of $\vartheta_{prox}$, the following equation can be used to find $q_{ins}$:

$$q_{ins} = -\overline{p}_{3/v} \cdot \hat{k} - \frac{L_1 \cos \theta_{prox}}{\frac{\pi}{2} - \theta_{prox}}, \qquad \text{Eqn 12}$$

where $\hat{k}$ is the unit vector in the z direction and $\overline{p}_{3/v} \cdot \hat{k}$ is the dot product of the vector $\overline{p}_{3/v}$, and the unit vector $\hat{k}$.

The above configuration variables calculated for the end effector position and orientation signals The above configuration variables are calculated for the end effector position and orientation signals $\overset{\triangleright}{P}_{EENEW}$ and $R_{EENEW}$ at block 636 or $\overset{\triangleright}{P}_{EEpREv}$ and $R_{EEpREv}$ at block 642 of the process 306. The configuration variables generally define a pose of the positioning device 209 required to position the end effector 210 at the desired location and orientation in end effector workspace. Configuration variables are produced for each end effector 210 and 214 of the respective right and left side instruments 208 and 212. Two sets of configuration variables referred to as left and right configuration variables respectively are thus produced and transmitted by the motion control interface 258 to the instrument processor circuit 130 and used by the microprocessor 280 to generate drive control signals for spatially positioning the positioning device 209 and end effector 210 of the instrument 208 in the surgical workspace.

3D Spatial Positioning

Figure 13:
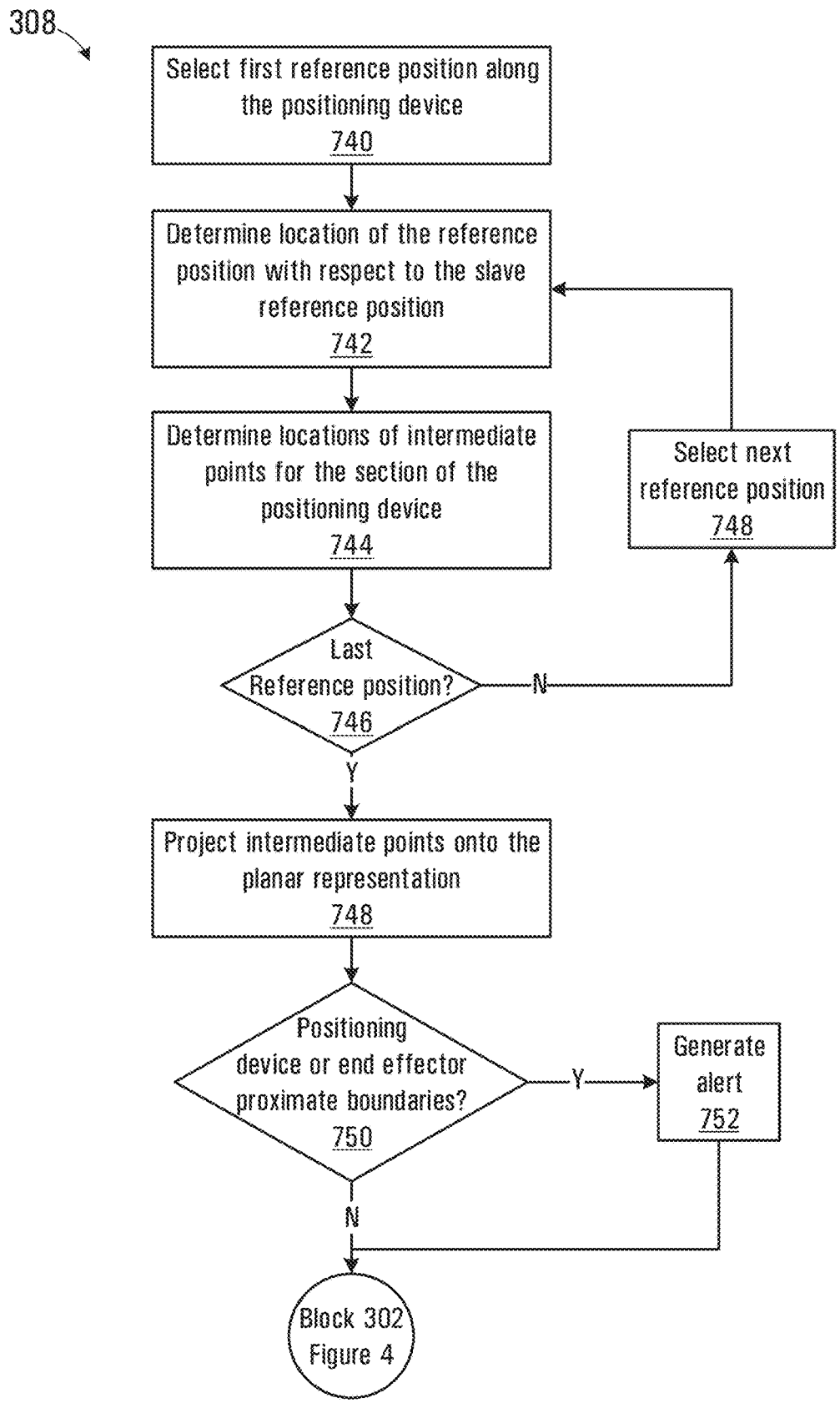
FIG. 13 is a flowchart depicting blocks of code for directing the workstation processor circuit shown in FIG. 3 to execute a process for generating display signals for displaying the graphical depictions shown in FIG. 5.

Further details of block 308 of the process 300 shown in FIG. 3 are shown in FIG. 13. Referring to FIG. 13, the process 308 includes blocks of codes executed by the workstation processor circuit 120 for generating display signals for displaying the graphical depictions 136 and 138 shown in FIG. 5. The process 308 uses the values of the configuration variables that were determined at block 306 to determine locations in the surgical workspace for points along the positioning devices 209 for the current inputs from the input device 110 and footswitch 134. The locations are determined relative to fixed slave reference position 552 within the surgical workspace. The process 308 generally involves determining theoretical locations for each of the reference points, namely the first position 704, second position 708, third position 706, fourth position 710 and the end effector position 560 in the surgical workspace. Once the theoretical location of each reference point is determined, the theoretical locations of various intermediate points along the positioning device 209 within the surgical workspace may be determined. Each of the sections 712, 714 of the s-segment 700, and the distal segment 702 of the positioning device 209 includes a plurality of vertebra 550 and centers of the vertebrae are spaced apart by the same distance. Since the s-segment 700 and distal segment 702 form smooth continuous constant-radius curves when bent, the theoretical location of the center of each vertebra can thus be calculated mathematically. The theoretical locations may be used to determine motion control signals used by the instrument processor circuit 130 to generate drive signals for the actual positioning of the instrument 208 in surgical workspace. The theoretical locations are also used by the workstation processor circuit 120 to generate the graphical depictions 136 and 138 shown in FIG. 5.

The process 308 begins at block 740, which directs the microprocessor 250 to select the first reference position (shown at 704 in FIG. 11) for processing. Block 742 then directs the microprocessor 250 to determine the location of the first position 704, which is spaced from the fixed slave reference position 552 by an unbendable portion of the positioning device 209 having length $q_{ins}$. The location of the first position 704 is thus determined by simple addition of the $q_{ins}$ configuration variable to the fixed slave reference position 552 in the $z_v$ axis. The location may be expressed in terms of a vector $\overline{p}_{1/v}$ from the fixed slave reference position 552 to the first position 704 within the surgical workspace.

Block 744 then directs the microprocessor 250 to determine locations of intermediate points along the first section 712 of the positioning device 209 (i.e. between the first position 704 and the second position 708). The location of the first position 704 determined at block 740 is used to determine locations of all vertebrae 550 in the first section 712 of the s-segment 700. For example in the embodiment shown in FIG. 11, assuming there are 15 vertebrae 550 in the first section 712 between the first position 704 and the second position 708, the center of the $n^{th}$ vertebrae will lie at a theoretical location that is at an intermediate point along the first section 220 calculated as:

$$\frac{n\theta_{prox}}{15}$$

relative to the first position 704. A vector from the first position 704 to the $n^{th}$ vertebra position may thus be determined and added to the vector $\overline{p}_{1/v}$ from the fixed slave reference position 552 to the first position 704 to determine the location of each of the n vertebrae of the first section 712 relative to the fixed slave reference position 552 in the surgical workspace.

Block 746 then directs the microprocessor 250 to determine whether all of the reference positions have been processed, and if not, the microprocessor is directed to block 748 where the next reference position is selected for processing. Block 748 then directs the microprocessor 250 back to block 742 and blocks 742 and 744 are repeated for each reference position.

The location of the second position 708 relative to the fixed slave reference position 552 may be determined from the configuration variables $q_{ins}$, $\vartheta_{prox}$, and $\delta_{prox}$. Determining a vector $\overline{p}_{2/v}$ from the fixed slave reference position 552 to the second position 708 provides a theoretical location of the second position in absolute terms within the surgical workspace. For the embodiment shown in FIG. 11, assuming again that there are 15 vertebrae in the second section 714, the center of the $n^{th}$ vertebrae of the second section would lie in an intermediate point along the second section. The angle at which the second section 222 is bent in the first bend plane $\delta_{prox}$ is equal and opposite to the angle $\vartheta_{prox}$ used for the calculations concerning the vertebrae of the first section 712. Therefore, an intermediate point of the $n^{th}$ vertebrae can be calculated as:

$$\frac{n(-\theta_{prox})}{15}$$

relative to the second position 708. A vector from the second position 708 to the n$^{th}$ vertebra position may thus be determined and added to the vector $\bar{p}_{2/v}$ from the slave reference position 552 to the second position 708 to provide the theoretical location of the n$^{th}$ vertebrae of the second section 714 in absolute terms within the positioning device workspace. This process may be repeated for each of the 15 vertebrae in the second section 714 of the s-segment 700 to find absolute locations for each vertebrae intermediate point within the surgical workspace relative to the fixed slave reference position 552.

The location of the third position 706 at the end of the s-segment 700 may be expressed in terms of the vector $\bar{p}_{3/v}$ having vector components as set out in Eqn 8a, 8b, and 8c above. The location of the third position 706 may be used as the reference point for determining the theoretical locations of all vertebrae 550 in the distal segment 702 using the method provided above. Assuming that there are 15 vertebrae in the distal segment 702, the center of the n$^{th}$ vertebrae would lie in an intermediate point that is along the distal segment. The angle at which the distal segment 702 is bent in the second bend plane $\delta_{dist}$ is $\vartheta_{dist}$. Therefore, an intermediate point of the n$^{th}$ vertebrae can be calculated as:

$$\frac{n\theta_{dist}}{15}$$

relative to the third position 706. A vector from the third position 706 to the n$^{th}$ vertebra position may thus be determined and added to the vector $\bar{p}_{3/v}$ to arrive at the theoretical location of the n$^{th}$ vertebrae in the distal segment 702 in absolute terms in the surgical workspace. This procedure is repeated for each of the 15 vertebrae in the distal segment 702 to find the theoretical location for each vertebrae intermediate point in the positioning device workspace in absolute terms, relative to the fixed slave reference position 552.

The location of the fourth position 710 may be determined from the vector $\bar{p}_{4/3}$ relative to the third position 706 having vector components as set out in Eqn 6a, 6b, and 6c above. Adding the vector $\bar{p}_{4/3}$ to the vector $\bar{p}_{3/v}$ from the fixed slave reference position 552 to the third position 234 will arrive at the theoretical location of the fourth position in absolute terms relative to the fixed slave reference position in the surgical workspace.

Finally, the theoretical location of the end effector position 560 may be determined as a vector $\bar{p}_{5/4}$ relative to the fourth position 710 according to vector component relations set out in Eqn 7a, 7b and 7c above. Adding the vector from the fourth position 710 to the end effector position 550 to the vector $\bar{p}_{4/3}$ and to the vector $\bar{p}_{3/v}$ from the fixed slave reference position 552 will arrive at the theoretical location of the end effector position 560 in absolute terms relative to the fixed slave reference position.

If at block 746, each of the reference positions along the positioning device 209 has been processed, the locations of a plurality of points along the 209 and end effector 210 will have been determined, thus defining the 3D spatial positioning of the instrument 208 in the surgical workspace.

The process 308 then continues at block 748, which directs the microprocessor 250 to generate a two-dimensional projection of the current 3D spatial position of the positioning device 208 to generate the area 412 representing the positioning device shown in the graphical depiction 136 of FIG. 5. Block 748 also directs the microprocessor 250 to generate a two-dimensional projection of the current 3D spatial position of the end effector 210 to generate the indicator 408 representing the end effector shown in FIG. 5. In one embodiment, the planar representation 136 is generated for a plane that is aligned with the $x_v$-$y_v$ plane (i.e. perpendicular to the $z_v$ axis) and the projection is generated from the $x_v$ and $y_v$ components of the location of each intermediate point along the positioning device 209 and end effector 210 (i.e. the $z_v$ components are set to zero).

The process 308 then continues at block 750, which directs the microprocessor 250 to determine whether any projected portion of the positioning device 209 is proximate the boundary 406 in FIG. 5 indicating that a constraint to further movement of the positioning device is active. Block 750 also directs the microprocessor 250 to determine whether any projected portion of the end effector 210 is proximate the boundary 402. If either of these conditions is detected, block 750 directs the microprocessor 250 to block 752.

Block 752 directs the microprocessor 250 to cause an active constraint alert to be generated. In one embodiment a visual alert may be generated by changing a color or displayed intensity of the boundary 402 or 406 or by displaying an alert symbol on the display 122. The alert may alternatively be displayed in the graphical depictions 136 and 138 overlaying the location of the indicators 412 and 414. In other embodiments an audible alert may be generated. Alternatively or additionally, the microprocessor 250 may cause the input device 110 to generate haptic feedback via the hand controller 112. Block 752 then directs the microprocessor 250 back to block 302 in FIG. 4.

If at block 750, the positioning device 209 and end effector 210 are not proximate any boundaries, the microprocessor 250 is directed back to block 302 in FIG. 4.

Depth

The instrument depth range 416 depiction shown in FIG. 5 is generated as follows. The depth range is taken along an axis 492 shown in FIG. 6, with the end 424 of the range corresponding to a maximum depth 494 of the end effector 210 within the area 488. The end 426 of the instrument depth range 416 corresponds to a minimum depth 496 of the end effector 210 within area 488. The input device depth range 432 similarly corresponds to the portion of the hatched area 482 along the axis 492. The current depth indicator 420 is positioned on the instrument depth range 416 at a location corresponding to the z value of the end effector position 560. In one embodiment, the microprocessor 250 may cause an active constraint indication to be generated when the end effector 210 is proximate either ends 424 or 426 of the input device depth range. The alert may take the form of an audible alert, visual alert displayed on the display 122, or haptic feedback through the right input device 116 and hand controller 112. The instrument depth range 418 is similarly generated for the left side instrument 212.

Rotation

The instrument rotation range 440 shown in FIG. 5 is generated from the configuration variable y (i.e. the rotation of the end effector 210 about the axis $z_2$, as shown in FIG. 11). The "Δ" indicator represents the current rotation angle γ of the end effector 210, where the vertical line 444 is taken the reference corresponding to the right hand controller 112 being held in a generally un-rotated position. The instrument rotation range 440 has an extent that corresponds to the extent of the range of rotation provided by the hand controller 112. The instrument rotation range 440 may also be offset depending of the mapping between the input device workspace and the surgical workspace. For example, after the footswitch 134 has been depressed the hand controller 112 may be rotated prior to releasing the footswitch 134, thus offsetting the working rotational range, as shown in FIG. 5.

Positioning Device Active Constraints

Figure 14:
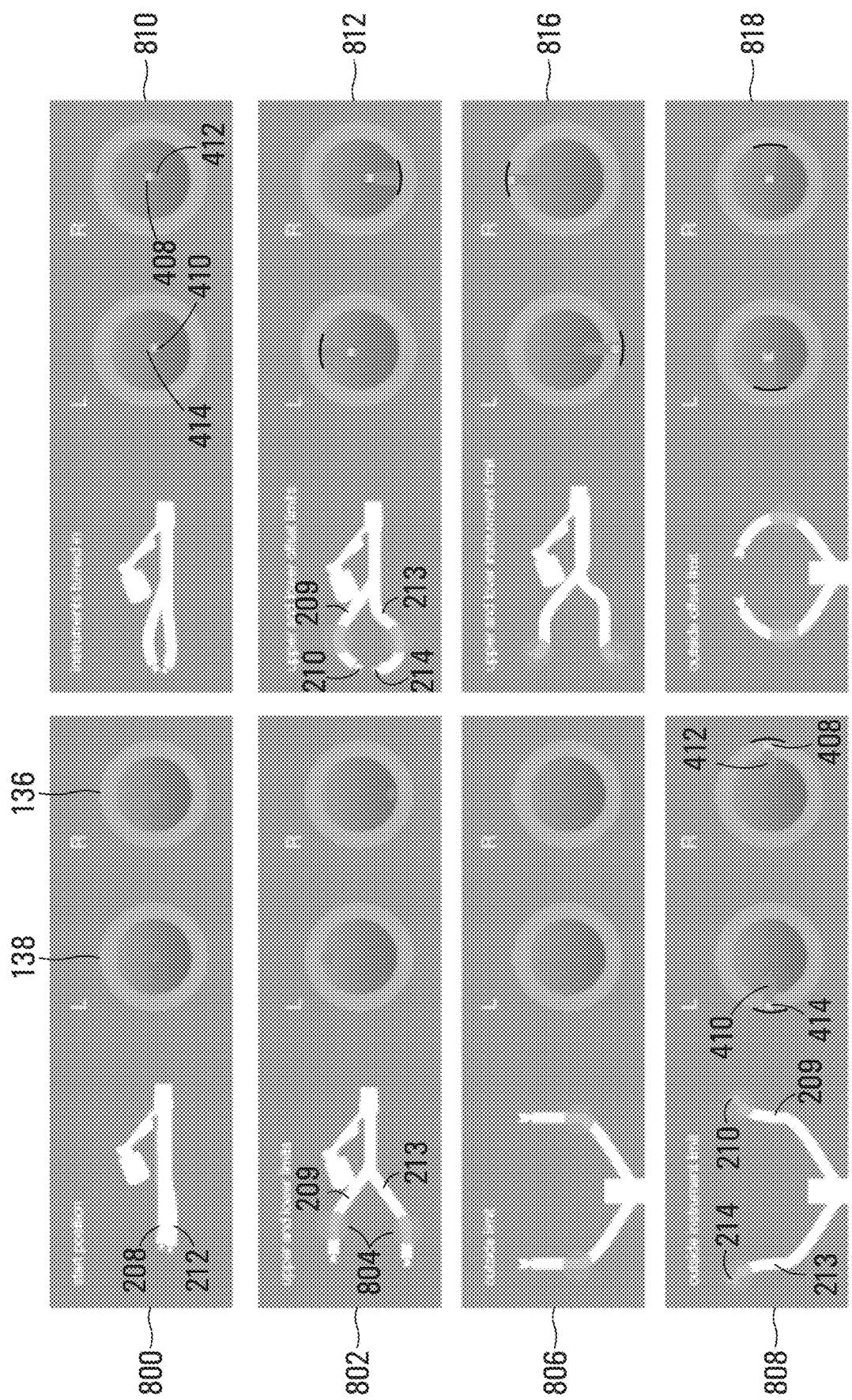
FIG. 14 are a series of examples of graphical depictions for positions of the left and right instruments.

The intermediate positions of the positioning device 209 of the right side instrument 208 calculated as described define the 3D location of the positioning device 209 of the instrument 208 within the surgical workspace (shown at 484 in FIG. 5). For each intermediate location of the vertebra 550, the microprocessor 250 determines whether the location is proximate a portion of the 3D boundary surface 485 of the surgical workspace 484. Examples of the graphical depictions for positions of the positioning device 209 of the instruments 208 and 212 are shown in FIG. 14. Referring to FIG. 14, the first example 800 shows the graphical depictions 136 and 138 for the instruments 208 and 212 in the start position after insertion where the positioning devices 209 and 213 are in a substantially straight position as shown in the side view of the instrument to the left of the depictions. The graphical depictions 136 and 138 depict the positioning devices 209 and 213 as respective dots located at the center.

In the next example 802, the positioning device 209 has been moved up and the positioning device 213 has been moved down and intermediate locations at 804 are determined by the microprocessor 250 to be proximate upper and lower portions of the boundary surface 485. The dots depicting the instruments 208 and 212 are shown at locations proximate the boundary. An alert may be generated by coloring portions of the boundary in a conspicuous color to indicate the condition to the surgeon.

An example of left/right limits for the positioning devices 209 and 213 are shown at 806. In the example shown at 808, the positioning devices 209 and 213 are positioned generally as in the example 806 but with the end effectors 210 and 214 turned outwardly. The end effectors 210 and 214 are located proximate the boundary surface 489 of the region 488 shown in FIG. 5 and are depicted by the indicators 408 and 410 respectively. The positioning devices 209 and 210 are represented by the areas 412 and 414 respectively. Alerts may be generated and depicted as conspicuously colored regions at the boundary surface 489 to indicate the condition to the surgeon.

An example 810 shows the instruments 208 and 212 slightly turned in so that the end effector indicators 408 and 410 and the areas 412 and 414 are visible. In the example 812, the end effectors 210 and 214 remain turned inwardly while the positioning devices 209 and 213 have reached the upper and lower limits as shown at 814. In example 816, the end effectors 210 and 214 have turned outwardly and are proximate respective upper and lower portions of the 3D boundary surface 489. In the final example 818, a similar situation shown in example 812 is shown for the left/right limits to positioning device movement.

While specific embodiments have been described and illustrated, such embodiments should be considered illustrative of the invention only and not as limiting the invention as construed in accordance with the accompanying claims.

What is claimed is:

1. A method for schematically representing a spatial position of an instrument used in a robotic surgery system, the instrument including an end effector coupled to an articulated arm configured to spatially position the end effector in a surgical workspace in response to input signals generated by movement of a hand controller of an input device in an input device workspace, the method comprising:

by a processor circuit, calculating a current three-dimensional spatial position of the instrument within the surgical workspace for current input signals received from the input device;

by the processor circuit, causing a display to display a graphical depiction of the surgical workspace, the graphical depiction including a planar representation comprising:
 an instrument movement region indicating a range of movement of the instrument within the surgical workspace, the instrument movement region representing a virtual depiction of the input device workspace and including a non-anatomical boundary indicating limitations to the range of movement of the instrument within the surgical workspace; and
 a two-dimensional projection of a current spatial position of the articulated arm and the end effector onto the planar representation;

by the processor circuit, receiving an enablement signal including an active state and an inactive state, the active state permitting movement of the instrument in response to the input signals and the inactive state locking the instrument in the current spatial position and inhibiting movement of the instrument to facilitate repositioning of the hand controller within the input device workspace;

by the processor circuit, in response to the enablement signal transitioning from the active state to the inactive state, causing the display to display a current hand controller position indicator on the graphical depiction as an offset from the two-dimensional projection of a current spatial position of the end effector; and by the processor circuit, in response to the enablement signal transitioning from the inactive state to the active state, causing the display to discontinue displaying the current hand controller position indicator while causing the display to continue displaying the planar representation including the instrument movement region and the two-dimensional projection of the current spatial position of the articulated arm and the end effector.

2. The method of claim 1 wherein in the two-dimensional projection the end effector is represented by an indicator and the articulated arm is represented by an area corresponding to two dimensional projected extents of at least a portion of the articulated arm.

3. The method of claim 1 further comprising generating the non-anatomical boundary by:
 defining a three-dimensional boundary within the surgical workspace; and
 generating a two-dimensional projection of the three-dimensional boundary onto the planar representation.

4. The method of claim 1 further comprising, by the processor circuit, in response to a determination that the instrument is proximate the non-anatomical boundary of the instrument movement region, causing the display to display an active constraint indication at the non-anatomical boundary.

5. The method of claim 1 wherein the robotic surgery system comprises a plurality of instruments within the surgical workspace and wherein displaying the graphical depiction comprises displaying a graphical depiction for each of the plurality of instruments.

6. The method of claim 1 wherein displaying the graphical depiction comprises displaying the graphical depiction at a peripheral region of the display.

7. The method of claim 1 wherein the graphical depiction further comprises:

an instrument depth range indicating limitations to axial movement of the instrument into the surgical workspace;

an indicator representing a current depth of the end effector within the instrument depth range; and an input device depth range representing a portion of the instrument depth range that is accessible by the instrument based on a current mapping between the input device workspace and the surgical workspace, wherein the input device workspace defines a limited range of the instrument depth range being accessible by the instrument.

8. The method of claim 7 further comprising, by the processor circuit, in response to a determination that the end effector is proximate an end of the input device depth range, causing the display to display an active constraint indication.

9. The method of claim 7 wherein the input device depth range is depicted as a hatched region superimposed on a depiction of the instrument depth range.

10. The method of claim 1 wherein the input signals include a rotation signal defining a current rotation of the hand controller, the rotation signal being operable to cause rotation of the end effector in the surgical workspace, and wherein the graphical depiction further comprises:

an instrument rotation range indicating limitations on rotational movement of the instrument;

an indicator representing a current rotation of the end effector; and an input device rotation range representing a portion of the instrument rotation range that is accessible for a current mapping between the input device workspace and the surgical workspace.

11. The method of claim 10 further comprising by the processor circuit:

in response to the enablement signal transitioning from the active state to the inactive state, causing the display to display a current hand controller rotation indicator on the graphical depiction as an offset from the indicator representing a current rotation of the end effector; and in response to the enablement signal transitioning from the inactive state to the active state, causing the display to discontinue displaying the current hand controller rotation indicator.

12. The method of claim 1 wherein the non-anatomical boundary is depicted as a hemisphere.

13. The method of claim 1 wherein the instrument movement region further includes at least one keep-out zone identifying a first region of the surgical workspace positioned within a second region of the surgical workspace circumscribed by the non-anatomical boundary, the at least one keep-out zone indicating a region that may not be accessed by the instrument.

14. An apparatus for schematically representing a spatial position of an instrument used in a robotic surgery system, the instrument including an end effector coupled to an articulated arm configured to spatially position the end effector in a surgical workspace in response to input signals generated by movement of a hand controller of an input device in an input device workspace, the apparatus comprising:

a display; and a processor circuit configured to:

calculate a current three-dimensional spatial position of the instrument within the surgical workspace for current input signals received from the input device;

cause the display to display a graphical depiction of the surgical workspace on a display, the graphical depiction including a planar representation comprising:

an instrument movement region indicating a range of movement of the instrument within the surgical workspace, the instrument movement region representing a virtual depiction of the input device workspace and including a non-anatomical boundary indicating limitations to the range of movement of the instrument within the surgical workspace; and a two-dimensional projection of a current spatial position of the articulated arm and the end effector onto the planar representation;

receive an enablement signal, the enablement signal including an active state and an inactive state, the active state permitting movement of the instrument in response to the input signals and the inactive state locking the instrument in the current spatial position and inhibiting movement of the instrument to facilitate repositioning of the hand controller within the input device workspace;

in response to the enablement signal transitioning from the active state to the inactive state, cause the display to display a current hand controller position indicator on the graphical depiction as an offset from the two-dimensional projection of a current spatial position of the end effector; and in response to the enablement signal transitioning from the inactive state to the active state, cause the display to discontinue displaying the current hand controller position indicator while causing the display to continue displaying the planar representation including the instrument movement region and the two-dimensional projection of the current spatial position of the articulated arm and the end effector.

15. The apparatus of claim 14 wherein the processor circuit is configured to cause the display to display an active constraint indication at the non-anatomical boundary in response to a determination that the instrument is proximate the non-anatomical boundary of the instrument movement region.

16. The apparatus of claim 14 wherein the graphical depiction further comprises:

an instrument depth range indicating limitations to axial movement of the instrument into the surgical workspace;

an indicator representing a current depth of the end effector within the instrument depth range; and an input device depth range representing a portion of the instrument depth range that is accessible by the instrument based on a current mapping between the input device workspace and the surgical workspace, wherein the input device workspace defines a limited range of the instrument depth range being accessible by the instrument.

17. The apparatus of claim 16 wherein the processor circuit is configured to cause the display to display an active constraint indication in response to a determination that the end effector is proximate an end of the input device depth range.

18. The apparatus of claim 14 wherein the input signals include a rotation signal defining a current rotation of the hand controller, the rotation signal being operable to cause rotation of the end effector in the surgical workspace, and wherein the graphical depiction further comprises:

an instrument rotation range indicating limitations on rotational movement of the instrument;

an indicator representing a current rotation of the end effector; and an input device rotation range representing a portion of the instrument rotation range that is accessible for a current mapping between the input device workspace and the surgical workspace.

19. The apparatus of claim 18 wherein the processor circuit is further configured to:

in response to the enablement signal transitioning from the active state to the inactive state, cause the display to display a current hand controller rotation indicator on the graphical depiction as an offset from the indicator representing a current rotation of the end effector; and in response to the enablement signal transitioning from the inactive state to the active state, cause the display to discontinue display of current hand controller rotation indicator.

20. The apparatus of claim 14 wherein the instrument movement region further includes at least one keep-out zone identifying a first region of the surgical workspace positioned within a second region of the surgical workspace circumscribed by the non-anatomical boundary, the at least one keep-out zone indicating a region that may not be accessed by the instrument.

21. The method of claim 13 wherein the at least one keep-out zone is defined based on input received from an operator and patient imaging data.

22. A non-transitory computer readable medium storing instructions that, when executed by a processor circuit of a robotic surgery system, direct the processor circuit to represent a spatial position of an instrument used in a robotic surgery system, the instrument including an end effector coupled to a positioning device for spatially positioning the end effector in a surgical workspace in response to input signals generated by movement of a hand controller of an input device in an input device workspace, the instructions further directing the processor circuit to:

calculate a current three-dimensional spatial position of the instrument within the surgical workspace for current input signals received from the input device;

cause a display to display a graphical depiction of the surgical workspace, the graphical depiction including a planar representation comprising:

an instrument movement region indicating a range of movement of the instrument within the surgical workspace, the instrument movement region representing a virtual depiction of the input device workspace and including a non-anatomical boundary indicating limitations to the range of movement of the instrument within the surgical workspace; and a two-dimensional projection of a current spatial position of the positioning device and the end effector onto the planar representation;

receive an enablement signal including an active state and an inactive state, the active state permitting movement of the instrument in response to the input signals and the inactive state locking the instrument in the current spatial position and inhibiting movement of the instrument to facilitate repositioning of the hand controller within the input device workspace;

in response to the enablement signal transitioning from the active state to the inactive state, cause the display to display a current hand controller position indicator on the graphical depiction as an offset from the two-dimensional projection of a current spatial position of the end effector; and in response to the enablement signal transitioning from the inactive state to the active state, cause the display to discontinue displaying the current hand controller position indicator while causing the display to continue displaying the planar representation including the instrument movement region and the two-dimensional projection of the current spatial position of the positioning device and the end effector.

* * * * *

UNITED STATES PATENT AND TRADEMARK OFFICE
CERTIFICATE OF CORRECTION

PATENT NO. : 11,504,191 B2
APPLICATION NO. : 15/780593
DATED : November 22, 2022
INVENTOR(S) : McCloud et al.

It is certified that error appears in the above-identified patent and that said Letters Patent is hereby corrected as shown below:

In the Specification

Column 11, Line 49 (approx.), delete "$y_v$," and insert -- $y_v$, --.

Column 11, Line 63 (approx.), delete "zv," and insert -- zv --.

Column 12, Line 26, delete "zy" and insert -- zv --.

Column 16, Line 30 (approx.), delete "$\vec{P}_{EPREV}$" and insert -- $\vec{P}_{EEPREV}$ --.

Column 16, Line 53 (approx.), after "applicant's" delete "co pending".

Column 17, Line 45, delete "$z_v$," and insert -- $z_v$ --.

Column 19, Line 60, delete "γa tan 2($y_{2z}$,-$x_{2z}$)-$\delta_{dist}$" and insert -- γ=atan2 ($y_{2z}$,-$x_{2z}$)-$\delta_{dist}$ --.

Column 20, Line 5, delete "$-\bar{p}_{5/4}$" and insert -- $-\bar{p}_{5/4}$, --.

Column 20, Line 63, delete "0<$\vartheta_{prox}$<Π" and insert -- 0<$\vartheta_{prox}$<Π, --.

Column 21, Line 15, delete "$\bar{p}_{3/v}$," and insert -- $\bar{p}_{3/v}$ --.

Column 21, Line 16-17 (approx.), below "$\bar{k}$." delete "The above configuration variables calculated for the end effector position and orientation signals".

Column 21, Line 21 (approx.), delete "$\vec{P}_{EEpREv}$ and $R_{EEpREv}$" and insert -- $\vec{P}_{EEPREV}$ and $R_{EEPREV}$ --.

Column 24, Line 57, delete "y" and insert -- γ --.

Signed and Sealed this
Fourth Day of April, 2023

Katherine Kelly Vidal
*Director of the United States Patent and Trademark Office*